(12) United States Patent
Rothschild et al.

(10) Patent No.: US 7,169,558 B2
(45) Date of Patent: *Jan. 30, 2007

(54) DETECTION OF DISEASE RELATED GENES

(75) Inventors: Kenneth J. Rothschild, Newton, MA (US); Sanjay M. Sonar, Mumbai (IN); Jerzy Olejnik, Allston, MA (US)

(73) Assignee: The Trustees of Boston University, Boston, MA (US)

( * ) Notice: Subject to any disclaimer, the term of this patent is extended or adjusted under 35 U.S.C. 154(b) by 652 days.

This patent is subject to a terminal disclaimer.

(21) Appl. No.: 10/401,251

(22) Filed: Mar. 27, 2003

(65) Prior Publication Data

US 2004/0033514 A1 Feb. 19, 2004

Related U.S. Application Data

(60) Continuation of application No. 09/943,120, filed on Aug. 30, 2001, now Pat. No. 6,566,070, which is a continuation of application No. 09/605,483, filed on Jun. 28, 2000, now abandoned, which is a continuation of application No. 09/307,579, filed on May 7, 1999, now Pat. No. 6,344,320, which is a continuation of application No. 09/290,325, filed on Apr. 12, 1999, now Pat. No. 6,210,941, which is a continuation of application No. 08/884,325, filed on Jun. 27, 1997, now Pat. No. 5,922,858, which is a division of application No. 08/240,511, filed on May 11, 1994, now Pat. No. 5,643,722.

(51) Int. Cl.
*C12Q 1/68* (2006.01)

(52) U.S. Cl. ............... 435/6; 435/7.1; 435/69.1; 435/71.1; 435/91.1; 435/91.2; 435/212

(58) Field of Classification Search ............... None
See application file for complete search history.

(56) References Cited

U.S. PATENT DOCUMENTS

| 5,643,722 A | * | 7/1997 | Rothschild et al. | ............ 435/6 |
| 6,566,070 B1 | * | 5/2003 | Rothschild et al. | ............ 435/6 |
| 6,949,341 B1 | * | 9/2005 | Rothschild et al. | ............ 435/6 |

* cited by examiner

*Primary Examiner*—James Ketter
(74) *Attorney, Agent, or Firm*—Medlen & Carroll, LLP

(57) ABSTRACT

The invention is directed to methods for the non-radioactive labeling, detection, quantitation and isolation of nascent proteins translated in a cellular or cell-free translation system. tRNA molecules are misaminoacylated with non-radioactive markers which may be non-native amino acids, amino acid analogs or derivatives, or substances recognized by the protein synthesizing machinery. Markers may comprise cleavable moieties, detectable labels, reporter properties wherein markers incorporated into protein can be distinguished from unincorporated markers, or coupling agents which facilitate the detection and isolation of nascent protein from other components of the translation system. The invention also comprises proteins prepared using misaminoacylated tRNAs which can be utflized in pharmaceutical compositions for the treatment of diseases and disorders in humans and other maninials, and kits which may be used for the detection of diseases and disorders.

23 Claims, 19 Drawing Sheets

⁻OOC—ALANINE-VALINE-TYROSINE-LYSINE-TRYPTOPHAN—$NH_3^+$

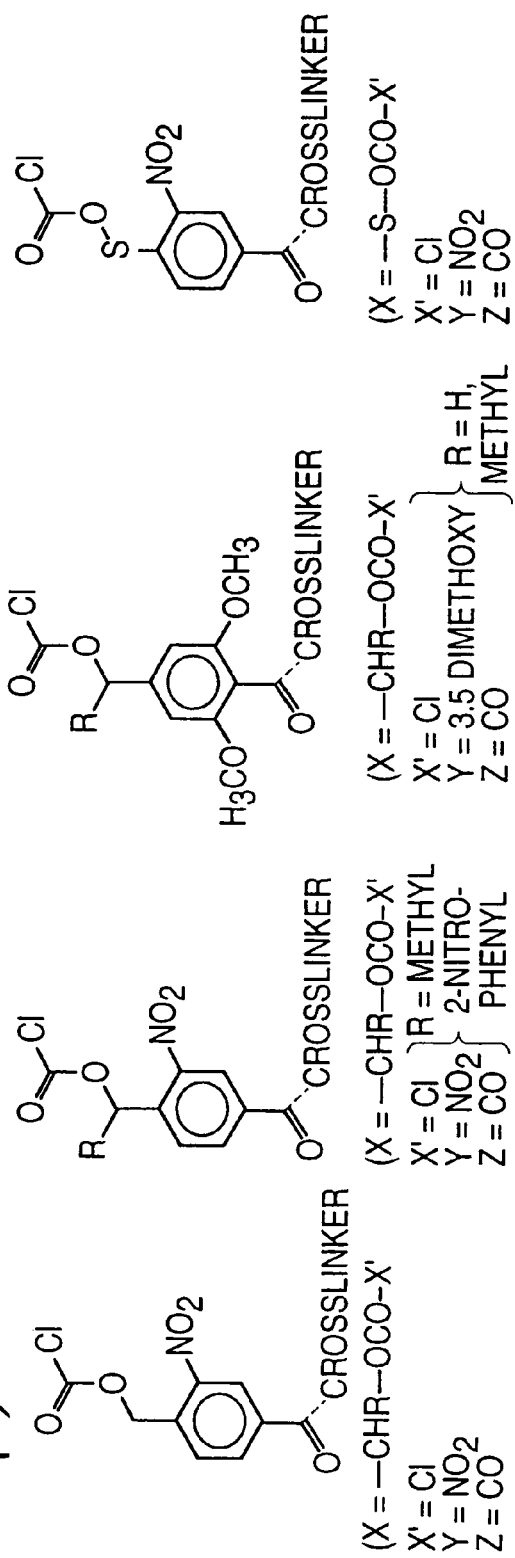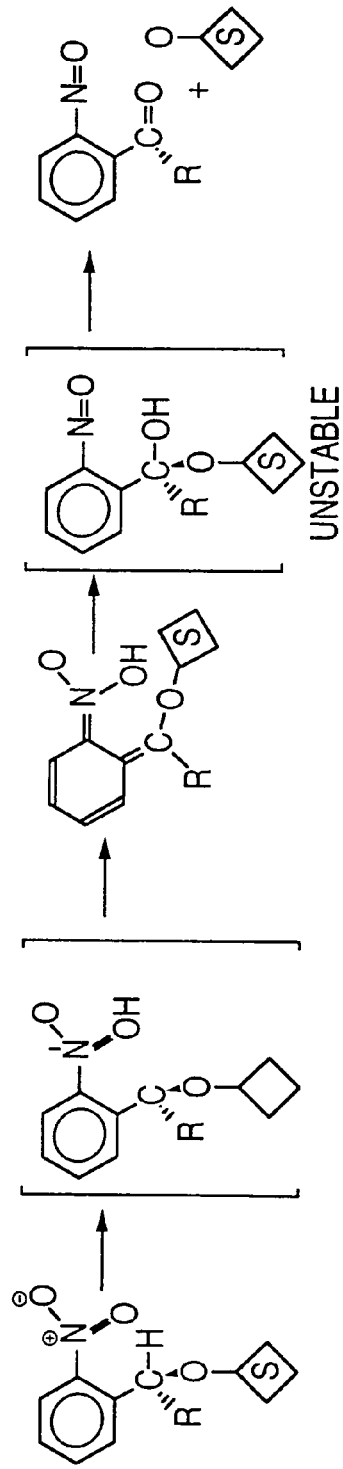
FIG. 6(A)
FIG. 6(B)

DETECTION OF DISEASE RELATED GENES

This is a Continuation of application(s) Ser. No. 09/943,120 filed on Aug. 30, 2001 now U.S. Pat. No. 6,566,070 which is a continuation of abandoned patent application Ser. No. 09/605,483 filed Jun. 28, 2000 which is a continuation of U.S. Pat. No. 6,344,320 Ser. No. 09/307,579 filed on May 7, 1999 which is a continuation of U.S. Pat. No. 6,210,941 Ser. No. 09/290,325 filed on Apr. 12, 1999 which is a continuation of U.S. Pat. No. 5,922,858 Ser. No. 08/884,325 filed Jun. 27, 1997 which is a divisional of U.S. Pat. No. 5,643,722 Ser. No. 08/240,511 filed May 11, 1994.

BACKGROUND OF THE INVENTION

1. Field of the Invention

This invention relates to non-radioactive markers that facilitate the detection of nascent proteins translated within cellular or cell-free translation systems. Nascent proteins containing these markers can be rapidly and efficiently isolated without the handling and disposal problems associated with radioactive reagents.

2. Description of the Background

Cells contain organelles, macromolecules and a wide variety of small molecules. Except for water, the vast majority of the molecules and macromolecules can be classified as lipids, carbohydrates, proteins or nucleic acids. Proteins are the most abundant cellular components and facilitate many of the key cellular processes. They include enzymes, antibodies, hormones, transport molecules and components for the cytoskeleton of the cell.

Figure 1A:
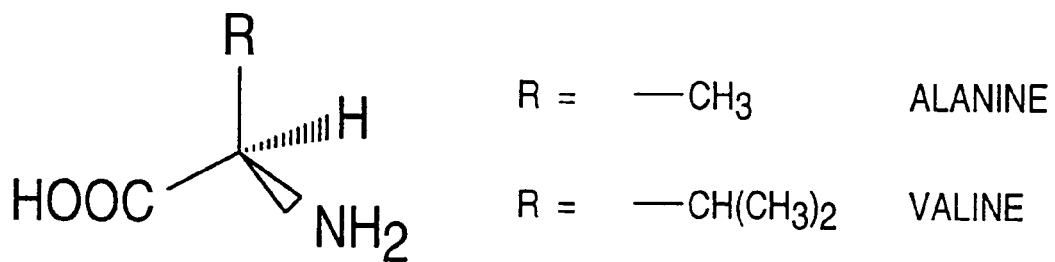

Proteins are composed of amino acids arranged into linear polymers or polypeptides. In living systems, proteins comprise over twenty common amino acids. These twenty or so amino acids are generally termed the native amino acids. At the center of every amino acid is the alpha carbon atom (Cα) which forms four bonds or attachments with other molecules (FIG. 1A). One bond is a covalent linkage to an amino group ($NH_2$) and another to a carboxyl group (COOH) which both participate in polypeptide formation. A third bond is nearly always linked to a hydrogen atom and the fourth to a side chain which imparts variability to the amino acid structure. For example, alanine is formed when the side chain is a methyl group (—$CH_3$) and a valine is formed when the side chain is an isopropyl group (—$CH(CH_3)_2$). It is also possible to chemically synthesize amino acids containing different side-chains, however, the cellular protein synthesis system, with rare exceptions, utilizes native amino acids. Other amino acids and structurally similar chemical compounds are termed non-native and are generally not found in most organisms.

Figure 1B:
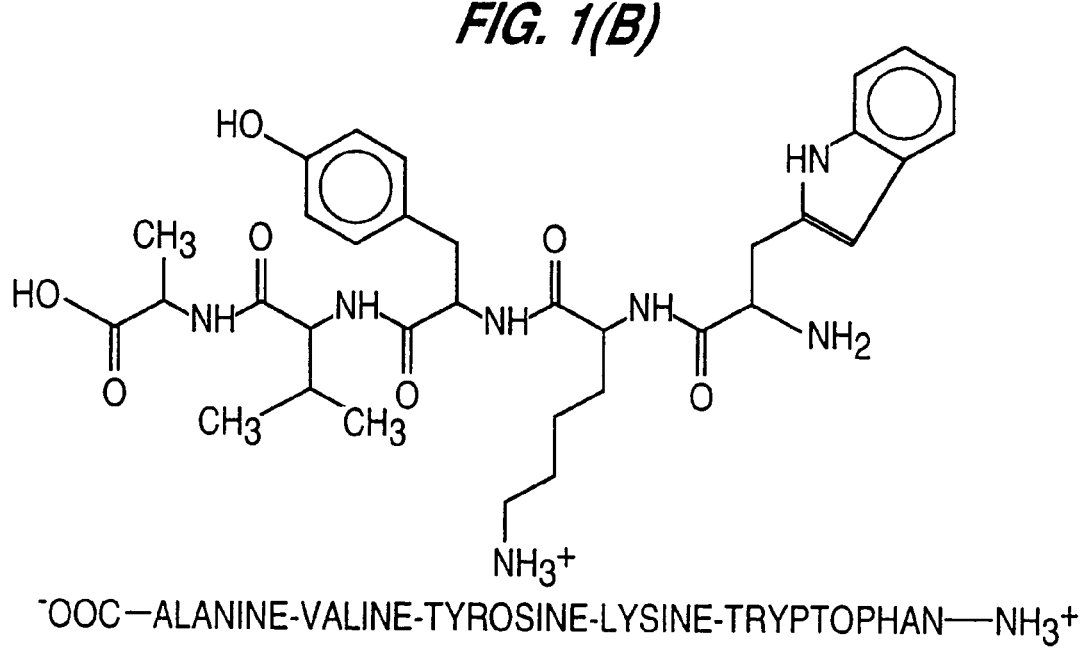

A central feature of all living systems is the ability to produce proteins from amino acids. Basically, protein is formed by the linkage of multiple amino acids via peptide bonds (~CO—NH~) such as the pentapeptide depicted in FIG. 1B. Key molecules involved in this process are messenger RNA (mRNA) molecules, transfer RNA (tRNA) molecules and ribosomes (rRNA-protein complexes). Protein translation normally occurs in living cells and in some cases can also be performed outside the cell in systems referred to as cell-free translation systems. In either system, the basic process of protein synthesis is identical. The extra-cellular or cell-free translation system comprises an extract prepared from the intracellular contents of cells. These preparations contain those molecules which support protein translation and depending on the method of preparation, post-translational events such as glycosylation and cleavages as well. Typical cells from which cell-free extracts or in vitro extracts are made are *Escherichia coli* cells, wheat germ cells, rabbit reticulocytes, insect cells and frog oocytes.

Both in vivo and in vitro syntheses involve the reading of a sequence of bases on a mRNA molecule. The mRNA contains instructions for translation in the form of triplet codons. The genetic code specifies which amino acid is encoded by each triplet codon. For each codon which specifies an amino acid, there normally exists a cognate tRNA molecule which functions to transfer the correct amino acid onto the nascent polypeptide chain. The amino acid tyrosine (Tyr) is coded by the sequence of bases UAU and UAC, while cysteine (Cys) is coded by UGU and UGC. Variability associated with the third base of the codon is common and is called wobble.

Figure 2:
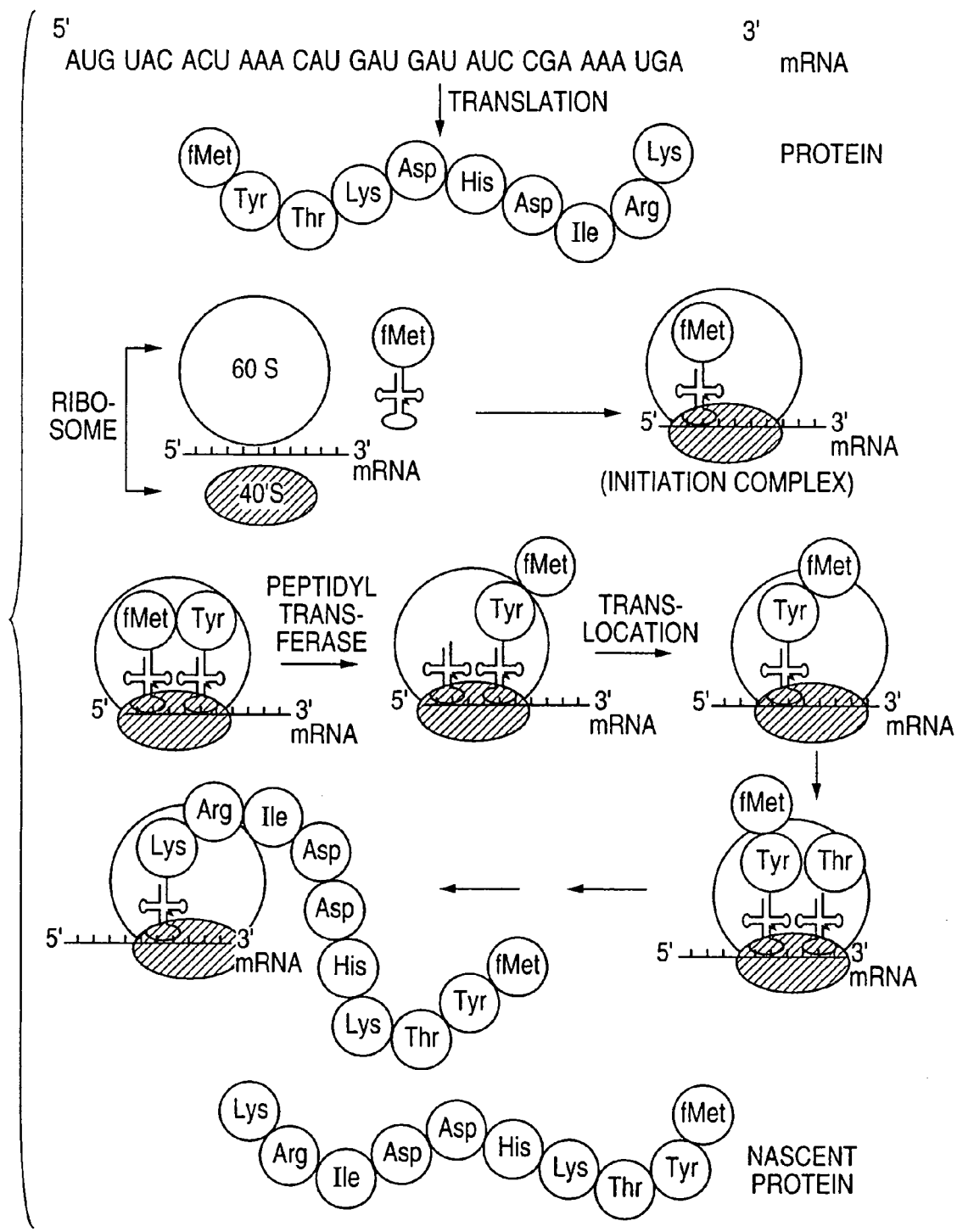

Translation begins with the binding of the ribosome to mRNA (FIG. 2). A number of protein factors associate with the ribosome during different phases of translation including initiation factors, elongation factors and termination factors. Formation of the initiation complex is the first step of translation. Initiation factors contribute to the initiation complex along with the mRNA and initiator tRNA (fmet and met) which recognizes the base sequence UAG. Elongation proceeds with charged tRNAs binding to ribosomes, translocation and release of the amino acid cargo into the peptide chain. Elongation factors assist with the binding of tRNAs and in elongation of the polypeptide chain with the help of enzymes like peptidyl transferase. Termination factors recognize a stop signal such as the base sequence UGA, in the message terminating polypeptide synthesis and releasing the polypeptide chain and the mRNA from the ribosome.

Figure 3A:
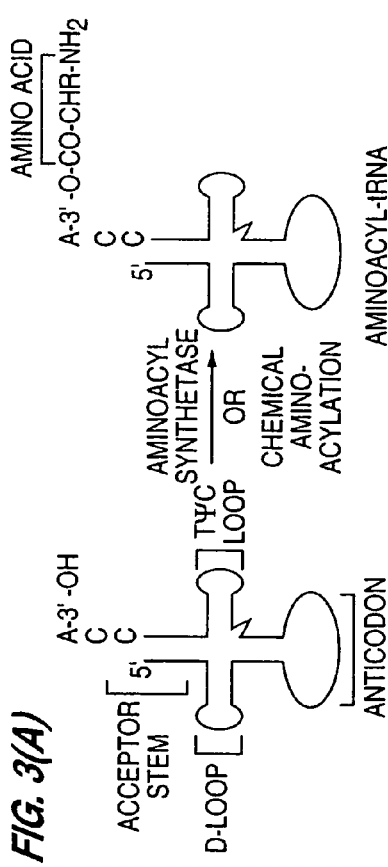

The structure of tRNA is often shown as a cloverleaf representation (FIG. 3A). Structural elements of a typical tRNA include an acceptor stem, a D-loop, an anticodon loop, a variable loop and a TΨC loop. Aminoacylation or charging of tRNA results in linking the carboxyl terminal of an amino acid to the 2'-(or 3'-) hydroxyl group of a terminal adenosine base via an ester linkage. This process can be accomplished either using enzymatic or chemical methods. Normally a particular tRNA is charged by only one specific native amino acid. This selective charging, termed here enzymatic aminoacylation, is accomplished by aminoacyl tRNA synthetases. A tRNA which selectively incorporates a tyrosine residue into the nascent polypeptide chain by recognizing the tyrosine UAC codon will be charged by tyrosine with a tyrosine-aminoacyl tRNA synthetase, while a tRNA designed to read the UGU codon will be charged by a cysteine-aminoacyl tRNA synthetase. These synthetases have evolved to be extremely accurate in charging a tRNA with the correct amino acid to maintain the fidelity of the translation process. Except in special cases where the non-native amino acid is very similar structurally to the native amino acid, it is necessary to use means other than enzymatic aminoacylation to charge a tRNA.

Molecular biologists routinely study the expression of proteins that are coded for by genes. A key step in research is to express the products of these genes either in intact cells or in cell-free extracts. Conventionally, molecular biologists use radioactively labeled amino acid residues such as $^{35}$S-methionine as a means of detecting newly synthesized proteins or so-called nascent proteins. These nascent proteins can normally be distinguished from the many other proteins present in a cell or a cell-free extract by first separating the proteins by the standard technique of gel electrophoresis and determining if the proteins contained in the gel possess the specific radioactively labeled amino acids. This method is simple and relies on gel electrophoresis, a widely available and practiced method. It does not require prior knowledge of the expressed protein and in general does not require the protein to have any special properties. In addition, the protein can exist in a denatured or unfolded form for detection by gel electrophoresis. Furthermore, more specialized techniques such as blotting to membranes and coupled enzymatic assays are not needed. Radioactive assays also have the advantage that the structure of the nascent protein is not altered or can be restored, and thus, proteins can be isolated in a functional form for subsequent biochemical and biophysical studies.

Radioactive methods suffer from many drawbacks related to the utilization of radioactively labeled amino acids. Handling radioactive compounds in the laboratory always involves a health risk and requires special laboratory safety procedures, facilities and detailed record keeping as well as special training of laboratory personnel. Disposal of radioactive waste is also of increasing concern both because of the potential risk to the public and the lack of radioactive waste disposal sites. In addition, the use of radioactive labeling is time consuming, in some cases requiring as much as several days for detection of the radioactive label. The long time needed for such experiments is a key consideration and can seriously impede research productivity. While faster methods of radioactive detection are available, they are expensive and often require complex image enhancement devices.

The use of radioactive labeled amino acids also does not allow for a simple and rapid means to monitor the production of nascent proteins inside a cell-free extract without prior separation of nascent from preexisting proteins. However, a separation step does not allow for the optimization of cell-free activity. Variables including the concentration of ions and metabolites and the temperature and the time of protein synthesis cannot be adjusted.

Radioactive labeling methods also do not provide a means of isolating nascent proteins in a form which can be further utilized. The presence of radioactivity compromises this utility for further biochemical or biophysical procedures in the laboratory and in animals. This is clear in the case of in vitro expression when proteins cannot be readily produced in vivo because the protein has properties which are toxic to the cell. A simple and convenient method for the detection and isolation of nascent proteins in a functional form could be important in the biomedical field if such proteins possessed diagnostic or therapeutic properties. Recent research has met with some success, but these methods have had numerous drawbacks.

Special tRNAs, such as tRNAs which have suppressor properties, suppressor tRNAs, have been used in the process of site-directed non-native amino acid replacement (SNAAR) (C. Noren et al., Science 244:182–188, 1989). In SNAAR, a unique codon is required on the mRNA and the suppressor tRNA, acting to target a non-native amino acid to a unique site during the protein synthesis (PCT WO90/05785) However, the suppressor tRNA must not be recognizable by the aminoacyl tRNA synthetases present in the protein translation system (Bain et al., Biochemistry 30:5411–21, 1991). Furthermore, site-specific incorporation of non-native amino acids is not suitable in general for detection of nascent proteins in a cellular or cell-free protein synthesis system due to the necessity of incorporating nonsense codons into the coding regions of the template DNA or the mRNA.

Products of protein synthesis may also be detected by using antibody based assays. This method is of limited use because it requires that the protein be folded into a native form and also for antibodies to have been previously produced against the nascent protein or a known protein which is fused to the unknown nascent protein. Such procedures are time consuming and again require identification and characterization of the protein. In addition, the production of antibodies and amino acid sequencing both require a high level of protein purity.

In certain cases, a non-native amino acid can be formed after the tRNA molecule is aminoacylated using chemical reactions which specifically modify the native amino acid and do not significantly alter the functional activity of the aminoacylated tRNA (Promega Technical Bulletin No. 182; tRNA$^{nacend}$TM: Non-radioactive Translation Detection System, September 1993). These reactions are referred to as post-aminoacylation modifications. For example, the $\epsilon$-amino group of the lysine linked to its cognate tRNA (tRNA$^{LYS}$), could be modified with an amine specific photoaffinity label (U. C. Krieg et al., Proc. Natl. Acad. Sci. USA 83:8604–08, 1986). These types of post-aminoacylation modifications, although useful, do not provide a general means of incorporating normative amino acids into the nascent proteins. The disadvantage is that only those normative amino acids that are derivatives of normal amino acids can be incorporated and only a few amino acid residues have side chains amenable to chemical modification. More often, post-aminoacylation modifications can result in the tRNA being altered and produce a non-specific modification of the $\alpha$-amino group of the amino acid (e.g. in addition to the $\epsilon$-amino group) linked to the tRNA This factor can lower the efficiency of incorporation of the non-native amino acid linked to the tRNA. Non-specific, post-aminoacylation modifications of tRNA structure could also compromise its participation in protein synthesis. Incomplete chain formation could also occur when the $\alpha$-amino group of the amino acid is modified.

In certain other cases, a nascent protein can be detected because of its special and unique properties such as specific enzymatic activity, absorption or fluorescence. This approach is of limited use since most proteins do not have special properties with which they can be easily detected. In many cases, however, the expressed protein may not have been previously characterized or even identified, and thus, its characteristic properties are unknown.

SUMMARY OF THE INVENTION

The present invention overcomes the problems and disadvantages associated with current strategies and designs and provides methods for the labeling, detection, quantitation and isolation of nascent proteins produced in a cell-free or cellular translation system without the use of radioactive amino acids or other radioactive labels.

One embodiment of the invention is directed to methods for detecting nascent proteins translated in a translation system. A tRNA molecule is aminoacylated with a cleavable marker to create a misaminoacylated tRNA. The misaminoacylated, or charged, tRNA can be formed by chemical, enzymatic or partly chemical and partly enzymatic techniques which place a cleavable marker into a position on the tRNA molecule from which it can be transferred into a growing peptide chain. Cleavable markers may comprise native amino acids with cleavable moieties, non-native amino acids, amino acid analogs or derivatives, detectable labels, coupling agents or combinations of these components. The misaminoacylated tRNA is introduced to the translation system such as a cell-free extract, the system is incubated and marker incorporated into nascent proteins.

These methods may be used to detect, isolate and quantitate such nascent proteins as recombinant gene products, gene fusion products, enzymes, cytokines, hormones, immunogenic proteins, human proteins, carbohydrate and lipid binding proteins, nucleic acid binding proteins, viral proteins, bacterial proteins, parasitic proteins and fragments and combinations thereof.

Another embodiment of the invention is directed to methods for labeling nascent proteins at their amino terminus. An initiator tRNA molecule, such as methionine-initiator tRNA or formylmethionine-initiator tRNA is misaminoacylated as before and introduced to a translation system. The system is incubated and marker is incorporate at the amino terminus of the nascent proteins. Nascent proteins containing marker can be detected, isolated and quantitated. Markers or parts of markers may be cleaved from the nascent proteins which substantially retain their native configuration and are functionally active.

Another embodiment of the invention is directed to methods for the detection of nascent proteins translated in a cellular or cell-free translation system using non-radioactive markers which have detectable electromagnetic spectral properties. As before, a non-radioactive marker is misaminoacylated to a tRNA molecule and the misaminoacylated tRNA is added to the translation system. The system is incubated to incorporate marker into the nascent proteins. Nascent proteins containing marker can be detected from the specific electromagnetic spectral property of the marker. Nascent proteins can also be isolated by taking advantage of unique properties of these markers or by conventional means such as electrophoresis, gel filtration, high-pressure or fast-pressure liquid chromatography, affinity chromatography, ion exchange chromatography, chemical extraction, magnetic bead separation, precipitation or combinations of these techniques.

Another embodiment of the invention is directed to the synthesis of nascent proteins containing markers-which have reporter properties. Reporter markers are chemical moieties which have detectable electromagnetic spectral properties when incorporated into peptides and whose spectral properties can be distinguished from unincorporated markers and markers attached to tRNA molecules. As before, tRNA molecules are misaminoacylated, this time using reported markers. The misaminoacylated tRNAs are added to a translation system and incubated to incorporate marker into the peptide. Reporter markers can be used to follow the process of protein translation and to detect and quantitate nascent proteins without prior isolation from other components of the protein synthesizing system.

Another embodiment of the invention is directed to compositions comprised of nascent proteins translated in the presence of markers, isolated and, if necessary, purified in a cellular or cell-free translation system. Compositions may further comprise a pharmaceutically acceptable carrier and be utilized as an immunologically active composition such as a vaccine, or as a pharmaceutically active composition such as a drug, for use in humans and other mammals.

Other embodiments and advantages of the invention are set forth, in part, in the description which follows and, in part, will be obvious from this description, or may be learned from the practice of the invention.

DESCRIPTIONS OF THE DRAWINGS

FIG. 1 Structure of (A) an amino acid and (B) a peptide (SEQ ID NO:1).

FIG. 2 Description of the molecular steps that occur during protein synthesis in a cellular or cell-free system (SEQ ID NOS:2–4).

FIG. 3 Structure of (A) a tRNA molecule and (B) approaches involved in the aminoacylation of tRNAs.

Figure 4:
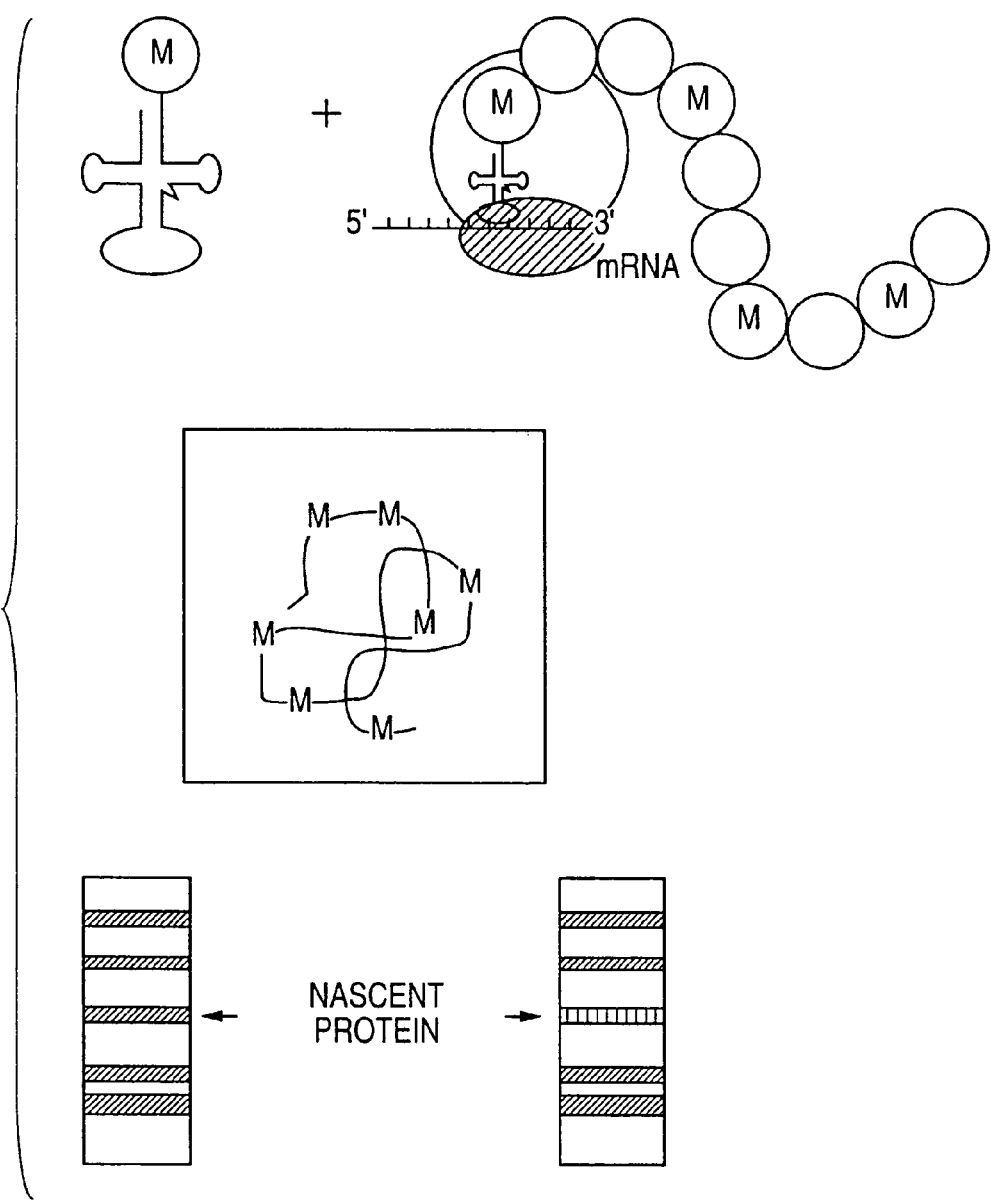

FIG. 4 Schematic representation of the method of detecting nascent proteins using fluorescent marker amino acids.

Figure 5:
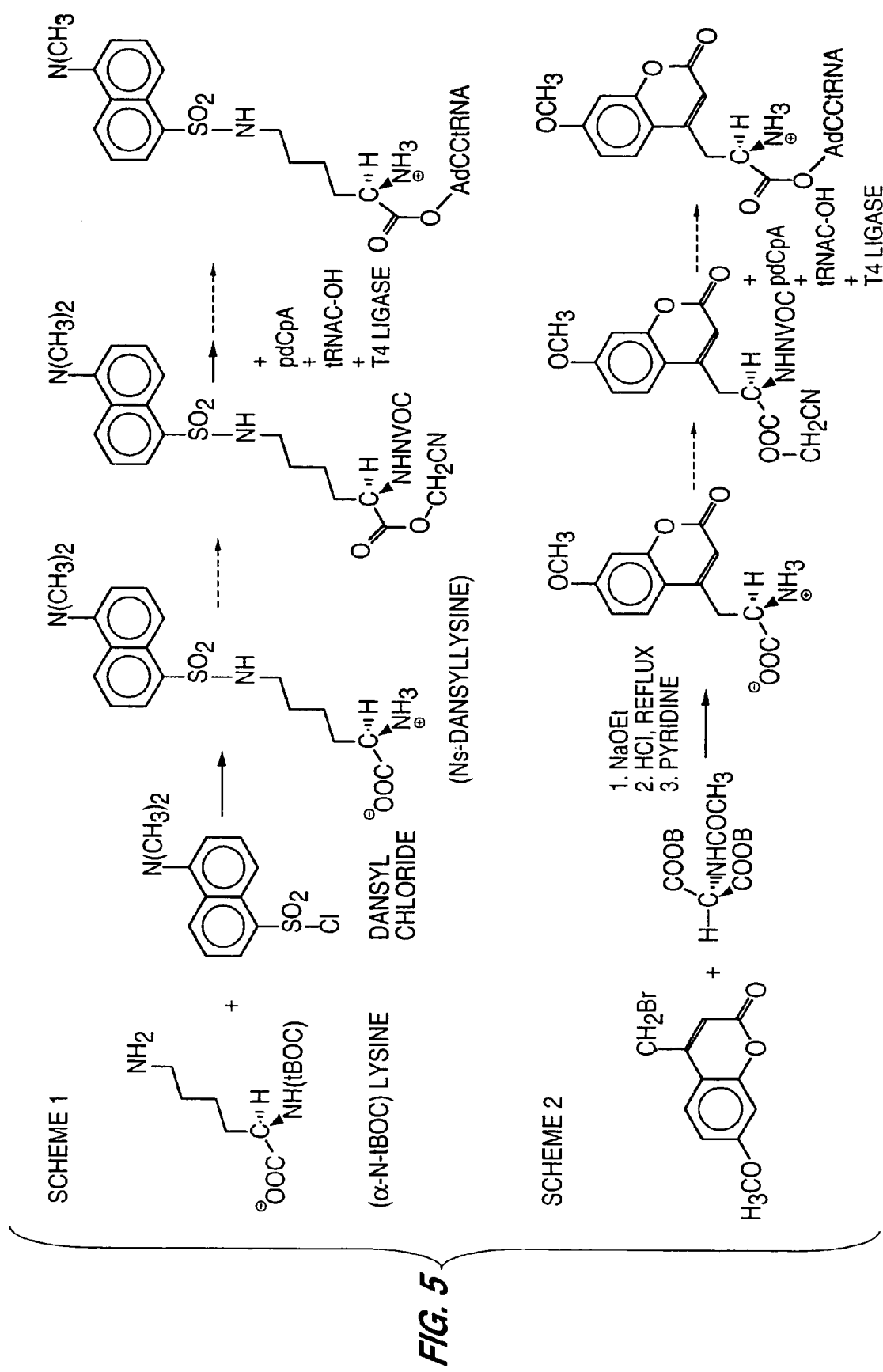

FIG. 5 Schemes for synthesis and misaminoacylation to tRNA of two different marker amino acids, dansyllysine (scheme 1) and coumarin (scheme 2), with fluorescent properties suitable for the detection of nascent proteins using gel electrophoresis and UV illumination.

FIG. 6(A) Chemical compounds containing the 2-nitrobenzyl moiety, and (B) cleavage of substrate from a nitrobenzyl linkage.

Figure 7:
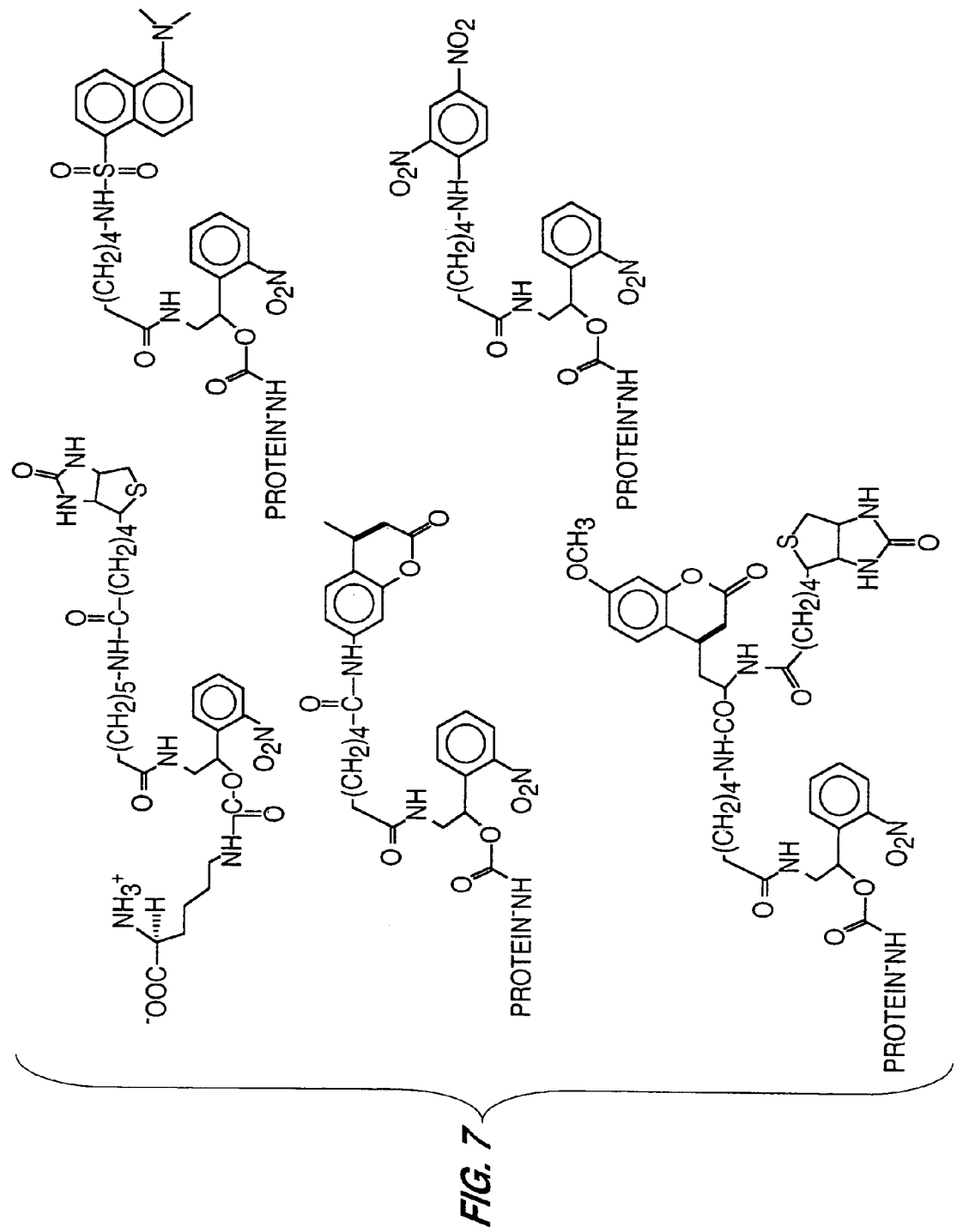

FIG. 7 Examples of photocleavable markers.

Figure 8A:
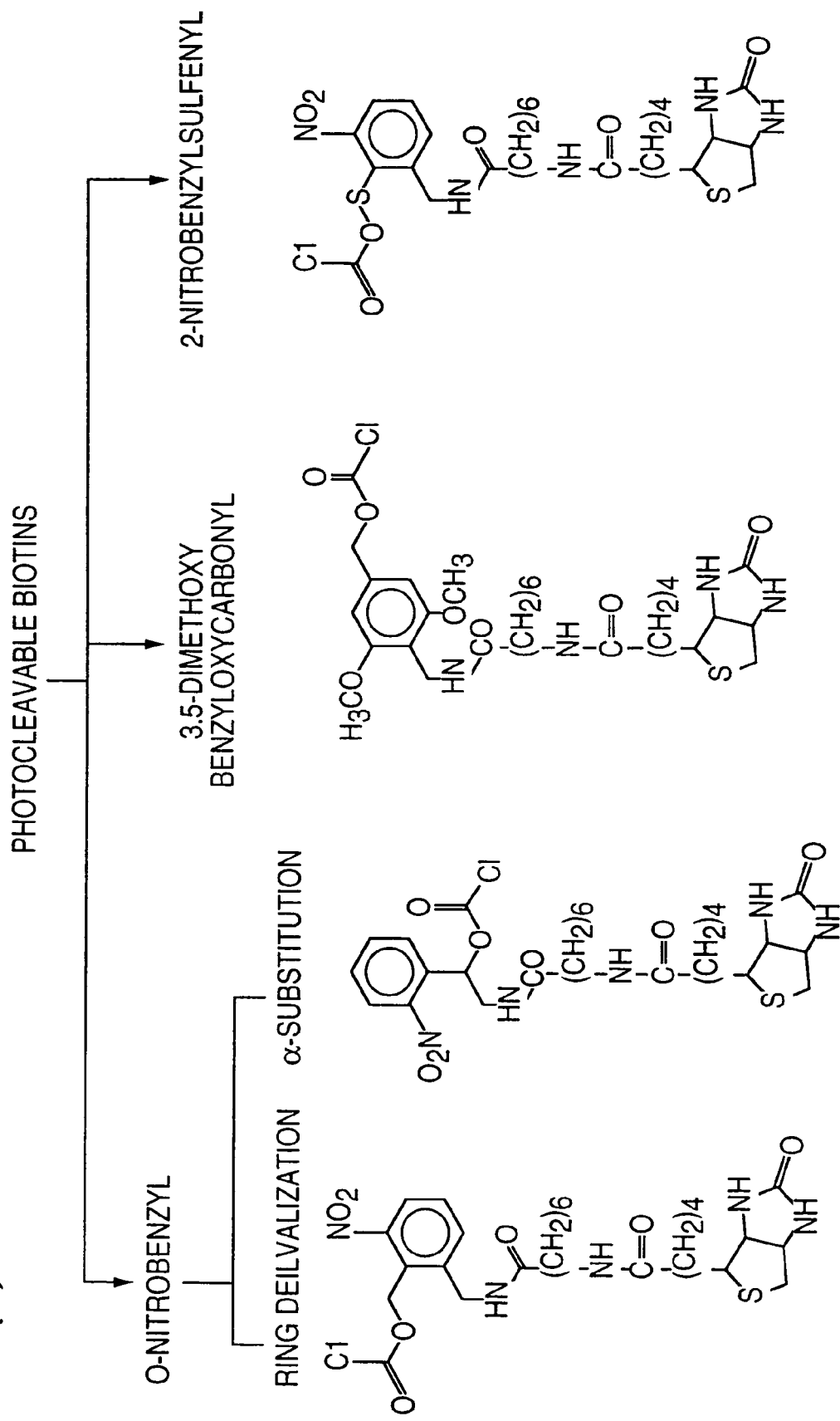

FIG. 8(A) Chemical variations of PCB, and (B) possible amino acid linkages.

Figure 9:
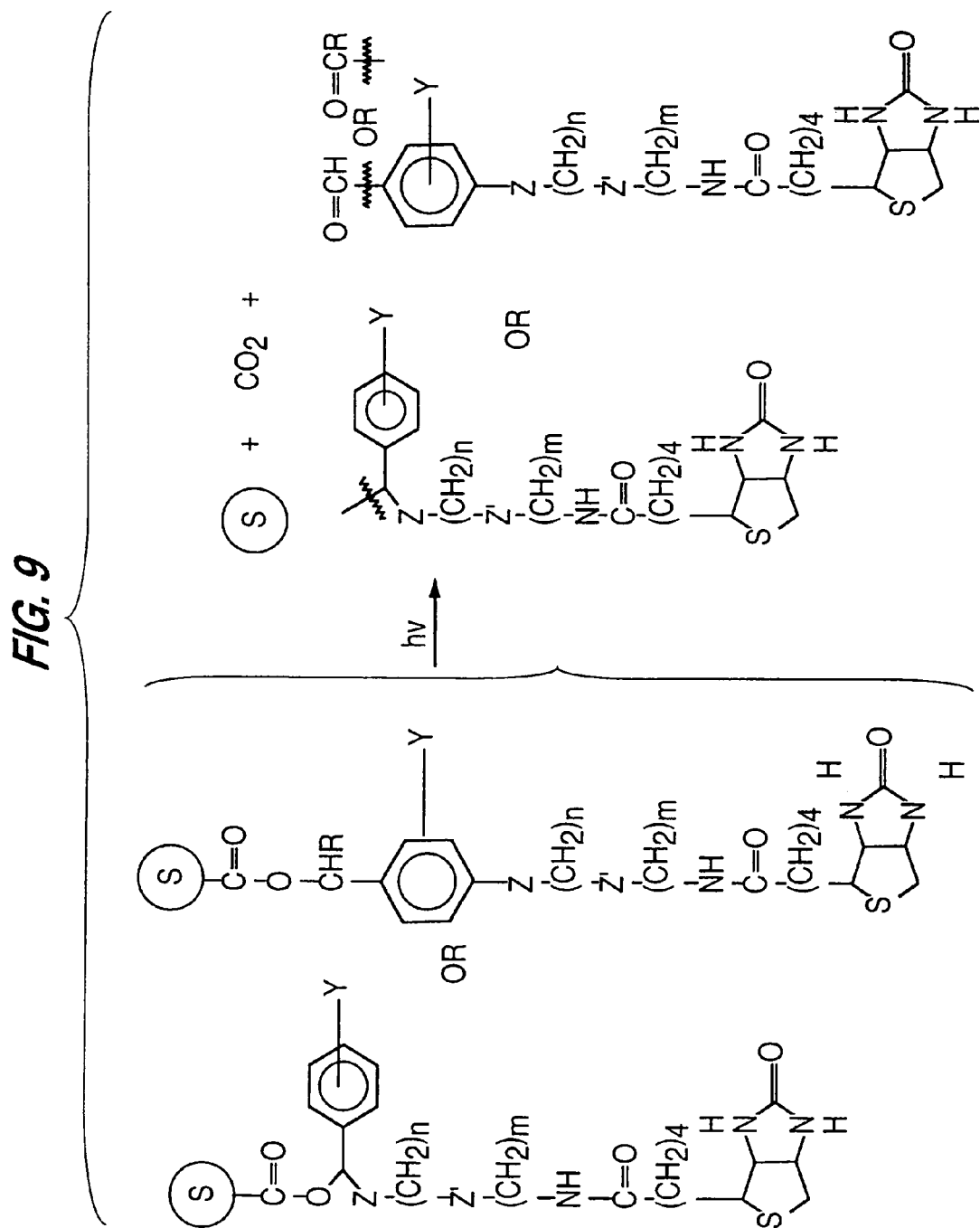

FIG. 9 Photolysis of PCB.

Figure 10:
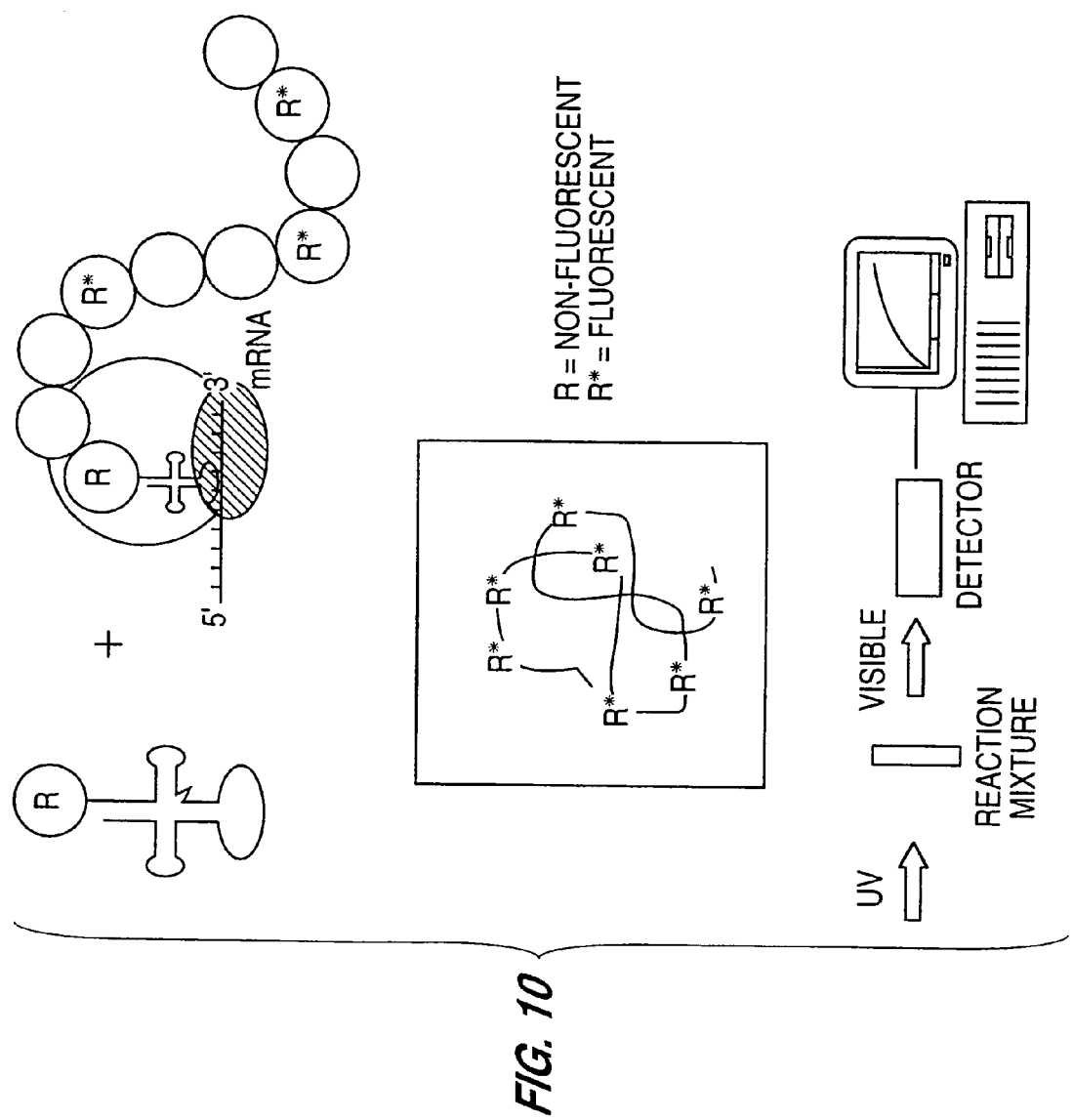

FIG. 10 Schematic representation of the method for monitoring the production of nascent proteins in a cell-free protein expression systems without separating the proteins.

Figure 11:
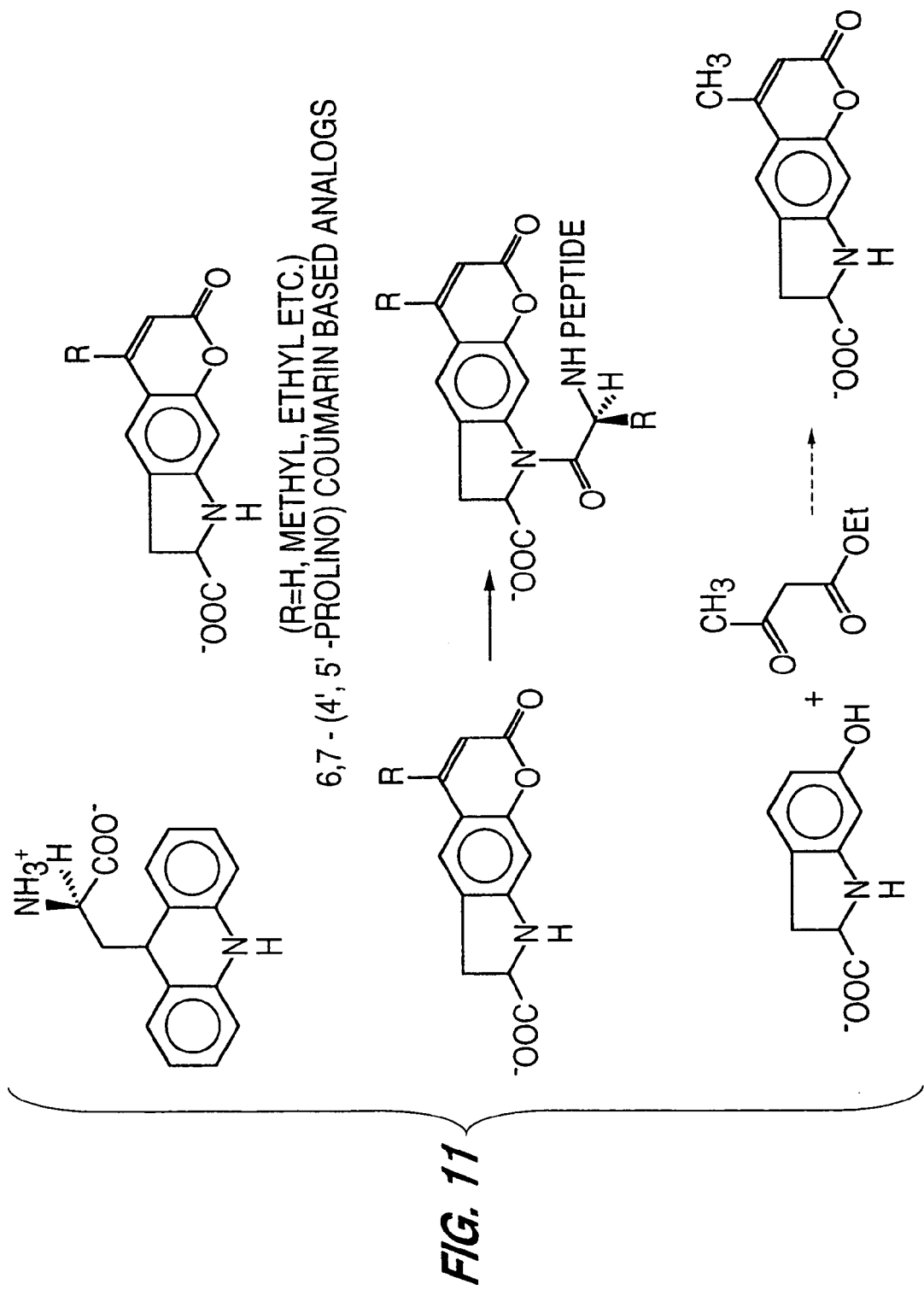

FIG. 11 Examples of non-native amino acids with reporter properties, participation of a reporter in protein synthesis, and synthesis of a reporter.

Figure 12:
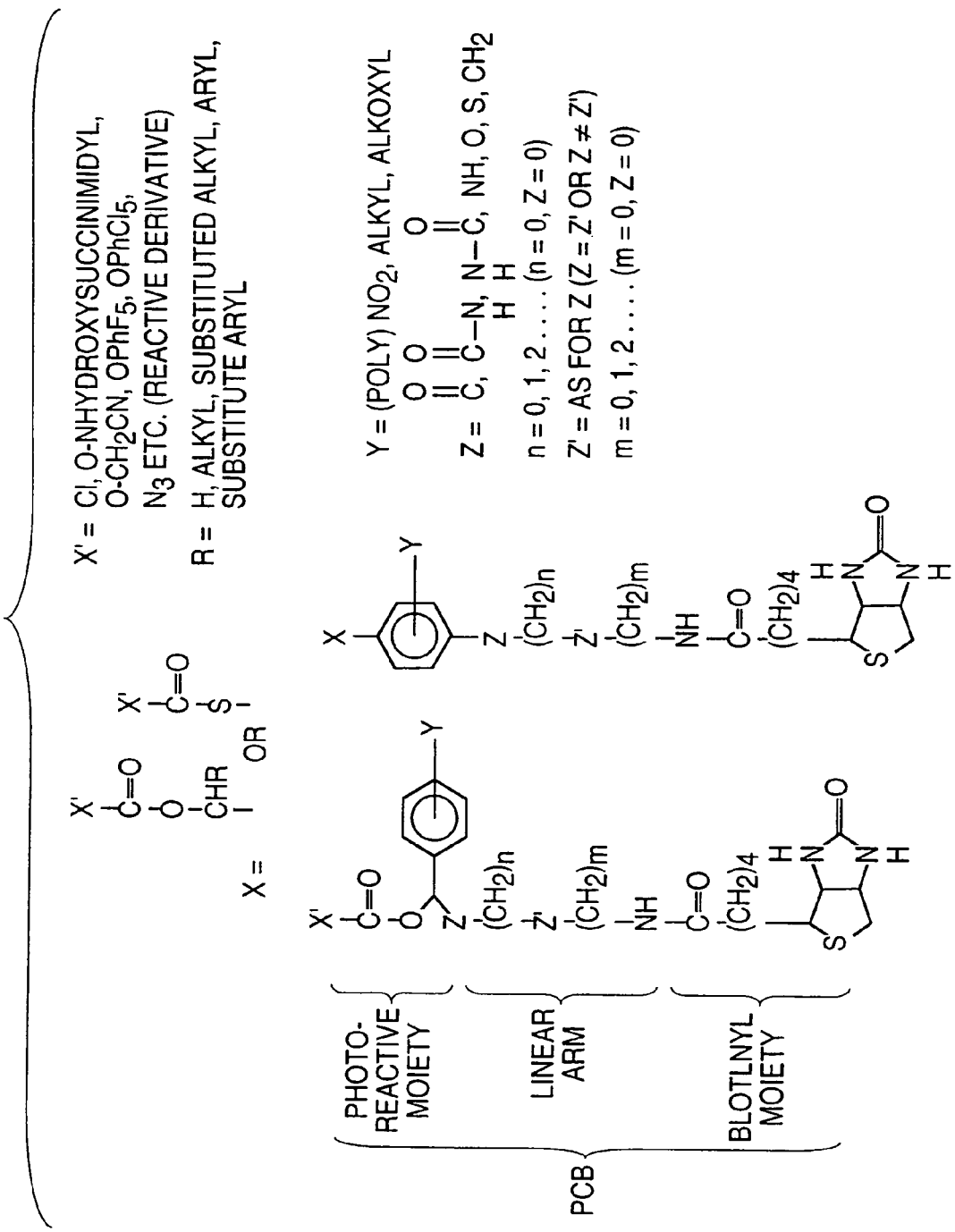

FIG. 12 Structural components of photocleavable biotin.

Figure 13:
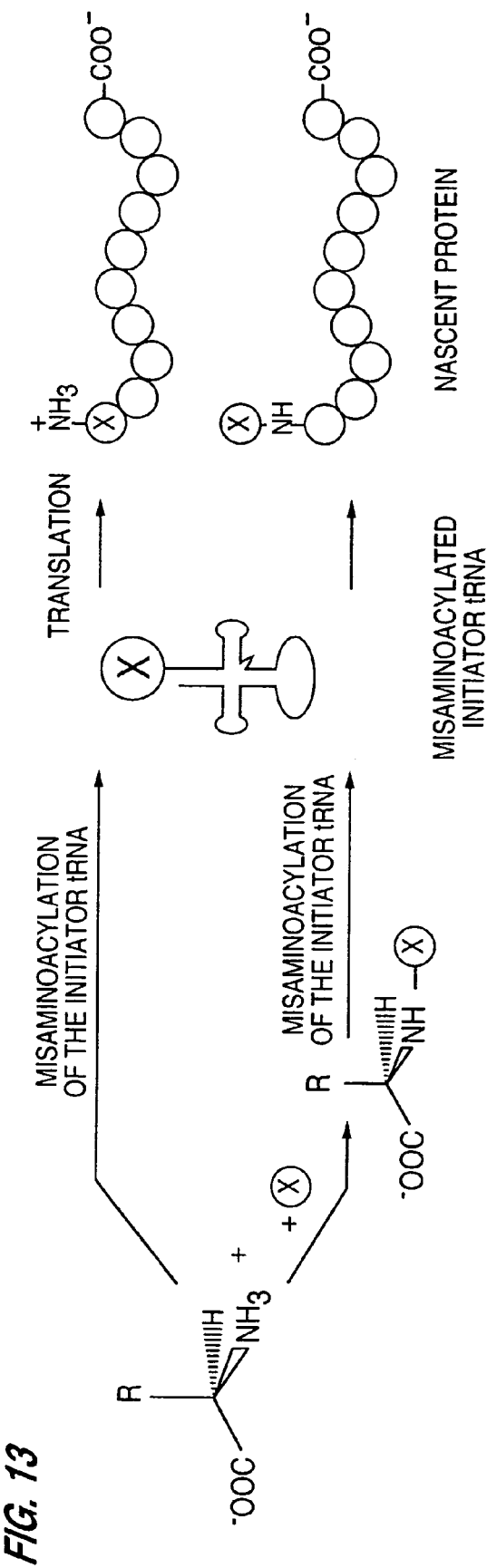

FIG. 13 Schematic representation of the method for introduction of markers at the N-termini of nascent proteins.

Figure 14:
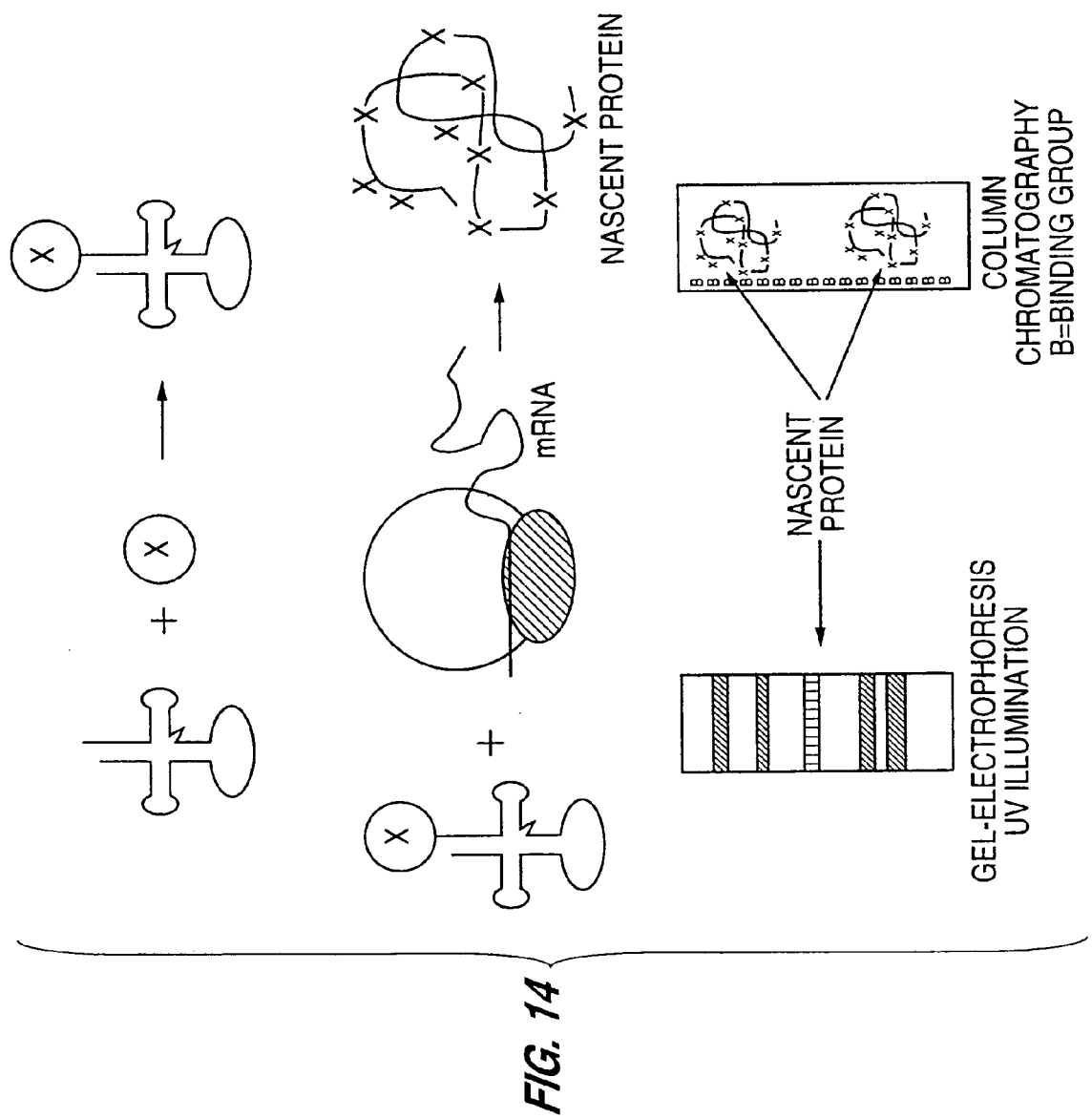

FIG. 14 Description of the method of detection and isolation of marker in nascent proteins.

Figure 15:
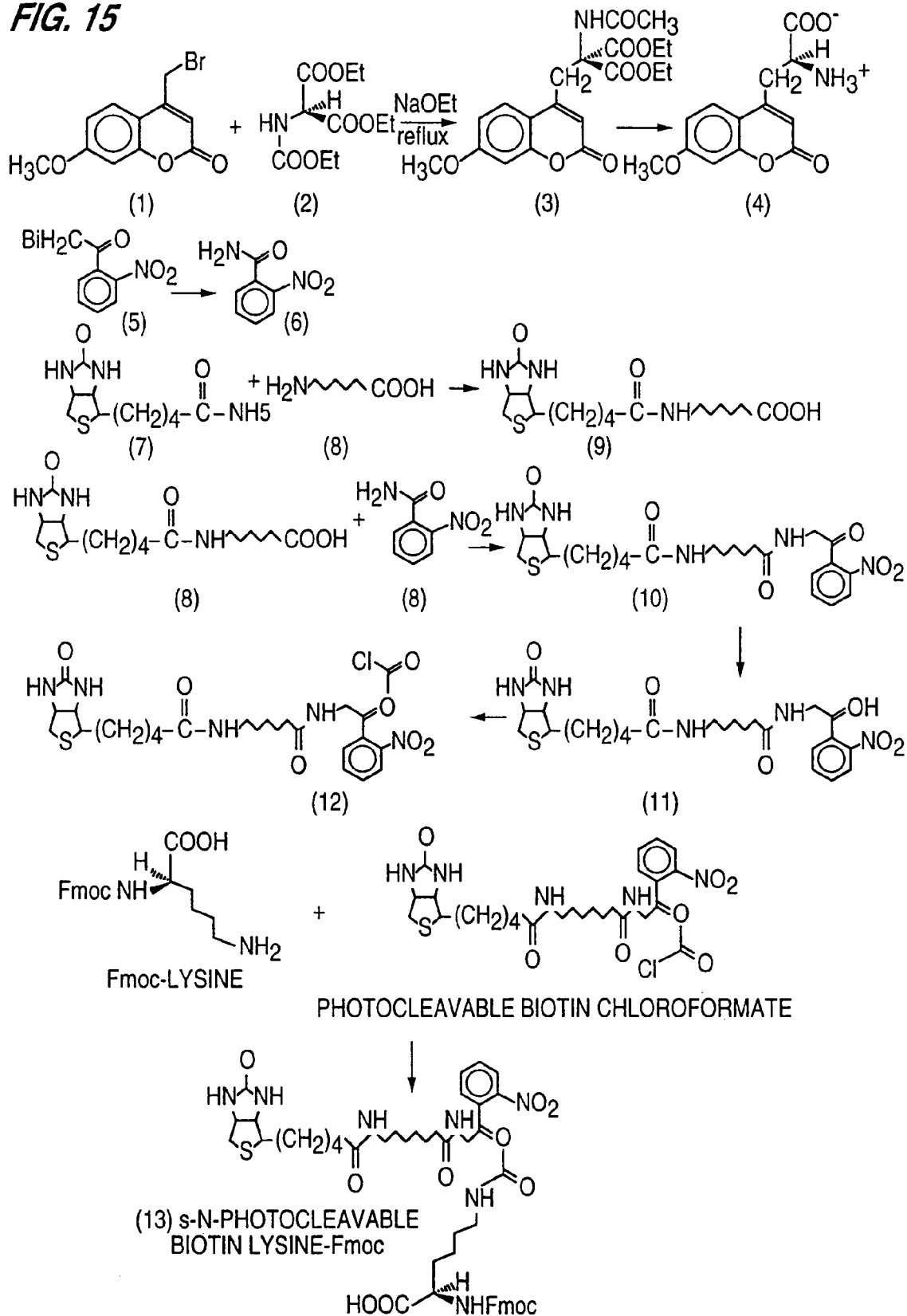

FIG. 15 Steps in the synthesis of PCB-lysine.

Figure 16:
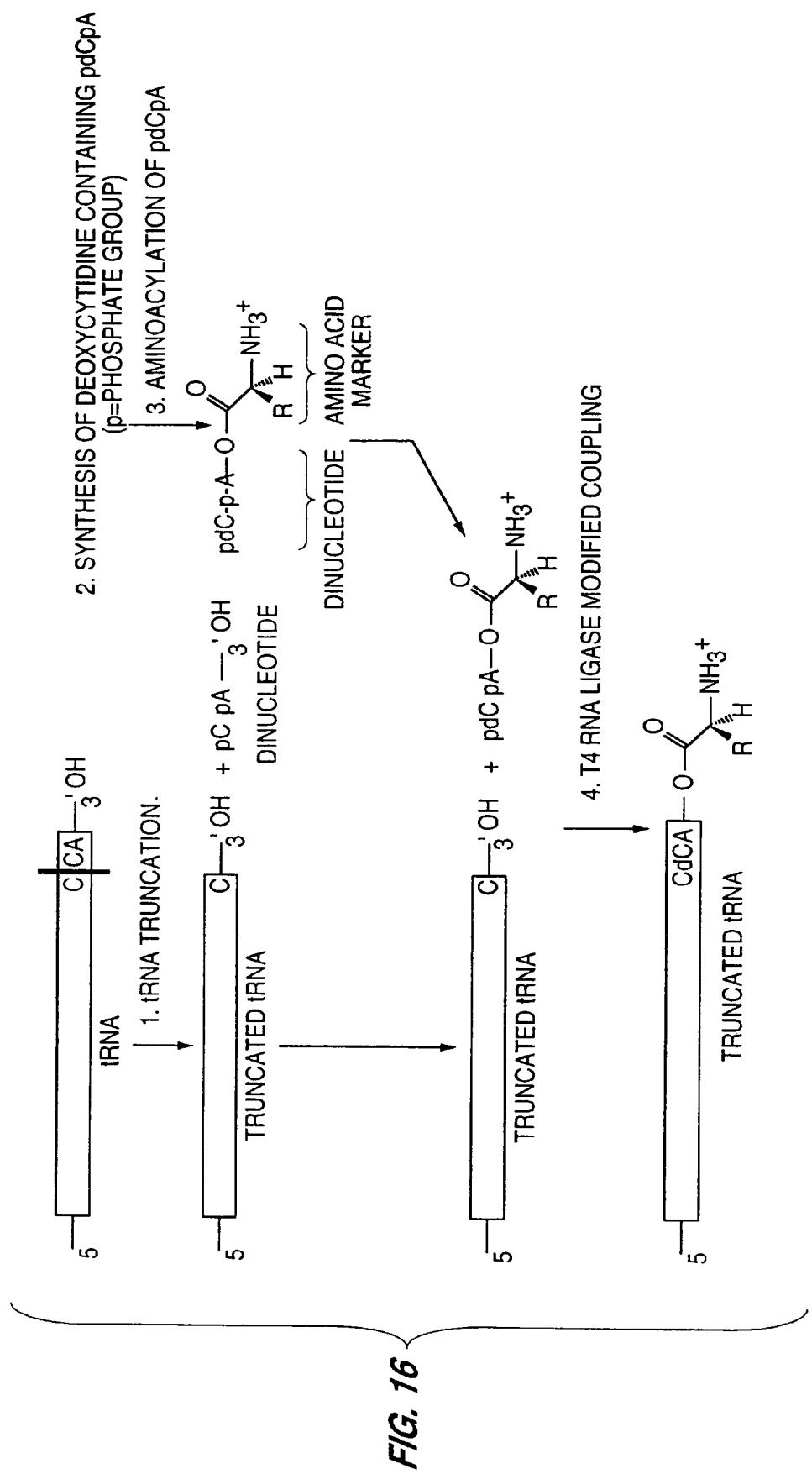

FIG. 16 Experimental strategy for the misaminoacylation of tRNA.

Figure 17:
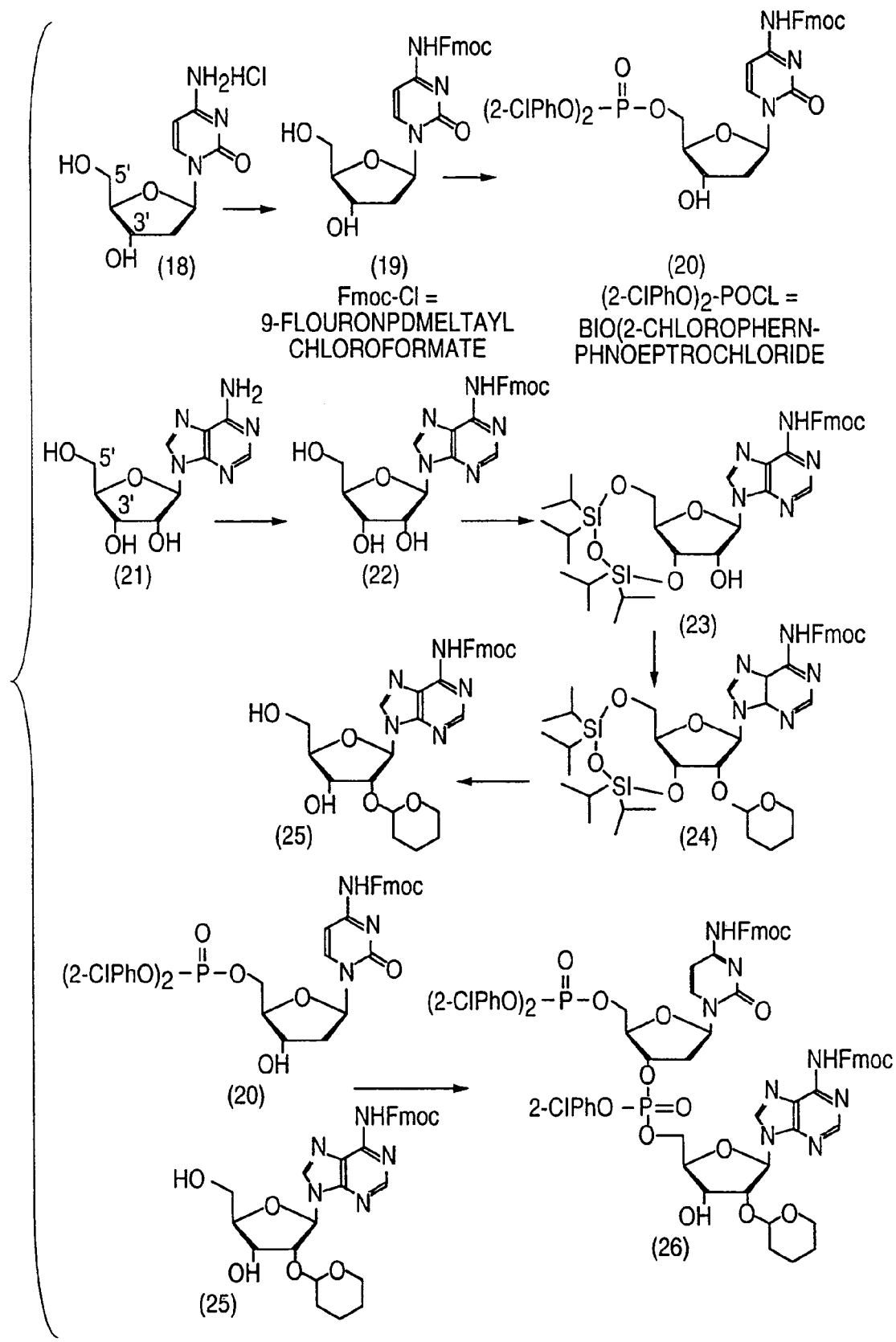

FIG. 17 Dinucleotide synthesis including (i) deoxycytidine protection, (ii) adenosine protection, and (iii) dinucleotide synthesis.

Figure 18:
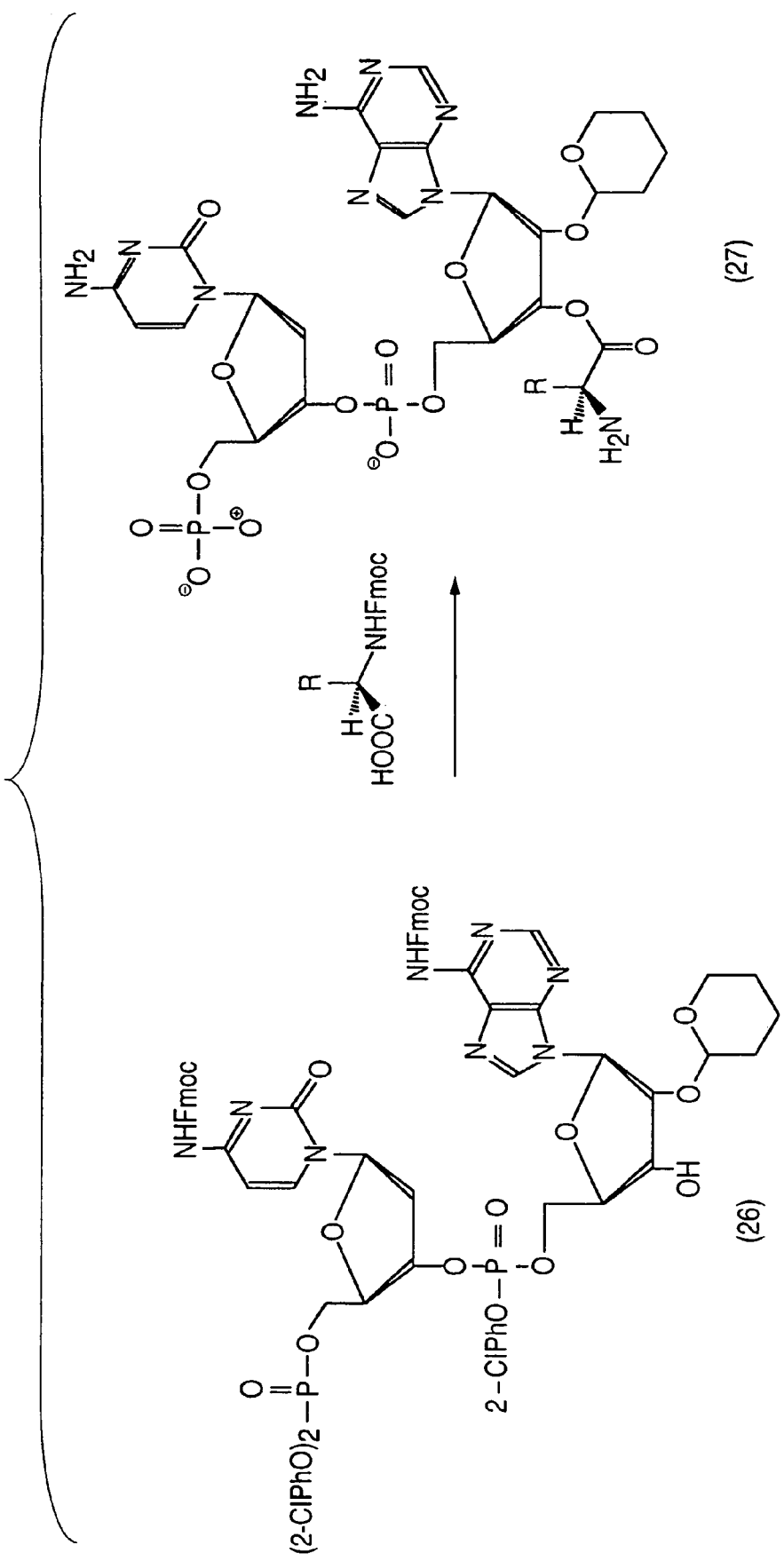

FIG. 18 Aminoacylation of a dinucleotide using marker amino acids.

DESCRIPTION OF THE INVENTION

As embodied and broadly described herein, the present invention comprises methods for the non-radioactive labeling and detection of the products of new or nascent protein synthesis, and methods for the isolation of these nascent proteins from preexisting proteins in a cellular or cell-free translation system. As radioactive labels are not used, there are no special measures which must be taken to dispose of waste materials. There is also no radioactivity danger or risk which would prevent further utilization of the translation product as occurs when using radioactive labels and the resulting protein product may be used directly or further purified. In addition, no prior knowledge of the protein sequence or structure is required which would involve, for example, unique suppressor tRNAs. Further, the sequence of the gene or tRNA need not be determined. Consequently, the existence of non-sense codons or any specific codons in the coding region of the mRNA is not necessary. Any tRNA can be used, including specific tRNAs for directed labeling, but such specificity is not required. Unlike post-translational labeling, nascent proteins are labeled with specificity and without being subjected to post-translational modifications which may effect protein structure or function.

One embodiment of the invention is directed to a method for labeling nascent proteins synthesized in a translation system. These proteins are labeled while being synthesized with detectable markers which are incorporated into the peptide chain. Markers which are aminoacylated to tRNA molecules, may comprise native amino acids, non-native amino acids, amino acid analogs or derivatives, or chemical moieties. These markers are introduced into nascent proteins from the resulting misaminoacylated tRNAs during the translation process. Aminoacylation is the process whereby a tRNA molecule becomes charged. When this process occurs in vivo, it is referred to as natural aminoacylation and the resulting product is an aminoacylated tRNA charged with a native amino acid. When this process occurs through artificial means, it is called misaminoacylation and a tRNA charged with anything but a native amino acid molecule is referred to as a misaminoacylated tRNA.

According to the present method, misaminoacylated tRNAs are introduced into a cellular or cell-free protein synthesizing system, the translation system, where they function in protein synthesis to incorporate detectable marker in place of a native amino acid in the growing peptide chain. The translation system comprises macromolecules including RNA and enzymes, translation, initiation and elongation factors, and chemical reagents. RNA of the system is required in three molecular forms, ribosomal RNA (rRNA), messenger RNA (mRNA) and transfer RNA (tRNA). mRNA carries the genetic instructions for building a peptide encoded within its codon sequence. tRNAs contain specific anti-codons which decode the mRNA and individually carry amino acids into position along the growing peptide chain. Ribosomes, complexes of rRNA and protein, provide a dynamic structural framework on which the translation process, including translocation, can proceed. Within the cell individualized aminoacyl tRNA synthetases bind specific amino acids to tRNA molecules carrying the matching anticodon creating aminoacylated or charged tRNAs by the process of aminoacylation. The process of translation including the aminoacylation or charging of a tRNA molecule is described in *Molecular Cell Biology* (J. Darnell et al. editors, Scientific American Books, N.Y., N.Y. 1991), which is hereby specifically incorporated by reference. Aminoacylation may be natural or by artificial means utilizing native amino acids, non-native amino acid, amino acid analogs or derivatives, or other molecules such as detectable chemicals or coupling agents. The resulting misaminoacylated tRNA comprises a native amino acid coupled with a chemical moiety, non-native amino acid, amino acid derivative or analog, or other detectable chemicals. These misaminoacylated tRNAs incorporate their markers into the growing peptide chain during translation forming labeled nascent proteins which can be detected and isolated by the presence or absence of the marker.

Any proteins that can be expressed by translation in a cellular or cell-free translation system may be nascent proteins and consequently, labeled, detected and isolated by the methods of the invention. Examples of such proteins include enzymes such as proteolytic proteins, cytokines, hormones, immunogenic proteins, carbohydrate or lipid binding proteins, nucleic acid binding proteins, human proteins, viral proteins, bacterial proteins, parasitic proteins and fragments and combinations. These methods are well adapted for the detection of products of recombinant genes and gene fusion products because recombinant vectors carrying such genes generally carry strong promoters which transcribe mRNAs at fairly high levels. These mRNAs are easily translated in a translation system.

Translation systems may be cellular or cell-free, and may be prokaryotic or eukaryotic. Cellular translation systems include whole cell preparations such as permeabilized cells or cell cultures wherein a desired nucleic acid sequence can be transcribed to mRNA and the mRNA translated.

Cell-free translation systems are commercially available and many different types and systems are well-known. Examples of cell-free systems include prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors.

Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (mRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

tRNA molecules chosen for misaminoacylation with marker do not necessarily possess any special properties other than the ability to function in the protein synthesis system. Due to the universality of the protein translation system in living systems, a large number of tRNAs can be used with both cellular and cell-free reaction mixtures. Specific tRNA molecules which recognize unique codons, such as nonsense or amber codons (UAG), are not required.

Site-directed incorporation of the normative analogs into the protein during translation is also not required. Incorporation of markers can occur anywhere in the polypeptide and can also occur at multiple locations. This eliminates the need for prior information about the genetic sequence of the translated mRNA or the need for modifying this genetic sequence.

In some cases, it may be desirable to preserve the functional properties of the nascent protein. A subset of tRNAs which will incorporate markers at sites which do not interfere with protein function or structure can be chosen. Amino acids at the amino or carboxyl terminus of a polypeptide do not alter significantly the function or structure. tRNA molecules which recognize the universal codon for the initiation of protein translation (AUG), when misaminoacylated with marker, will place marker at the amino terminus. Prokaryotic protein synthesizing systems utilize initiator tRNA$^{fMet}$ molecules and eukaryotic systems initiator tRNA$^{Met}$ molecules. In either system, the initiator tRNA molecules are aminoacylated with markers which may be non-native amino acids or amino acid analogs or derivatives that possess marker, reporter or affinity properties. The resulting nascent proteins will be exclusively labeled at their amino terminus, although markers placed internally do not necessarily destroy structural or functional aspects of a protein. For example, a tRNA$^{Lys}$ may be misaminoacylated with the amino acid derivative dansyllysine which does not interfere with protein function or structure. In addition, using limiting amounts of misaminoacylated tRNAs, it is possible to detect and isolate nascent proteins having only a very small fraction labeled with marker which can be very useful for isolating proteins when the effects of large quantities of marker would be detrimental or are unknown.

tRNAs molecules used for aminoacylation are commercially available from a number of sources and can be prepared using well-known methods from sources including *Escherichia coli*, yeast, calf liver and wheat germ cells (Sigma Chemical; St. Louis, Mo.; Promega; Madison, Wis.; Boehringer Mannheim Biochemicals; Indianapolis, Ind.). Their isolation and purification mainly involves cell-lysis, phenol extraction followed by chromatography on DEAE-cellulose. Amino-acid specific tRNA, for example tRNA$^{fMet}$, can be isolated by expression from cloned genes and overexpressed in host cells and separated from total tRNA by techniques such as preparative polyacrylamide gel electrophoresis followed by band excision and elution in high yield and purity (Seong and RajBhandary, Proc. Natl. Acad. Sci. USA 84:334–338, 1987). Run-off transcription allows for the production of any specific tRNA in high purity, but its applications can be limited due to lack of post-transcriptional modifications (Bruce and Uhlenbeck, Biochemistry 21:3921, 1982).

Misaminoacylated tRNAs are introduced into the cellular- or cell-free protein synthesis system. In the cell-free protein synthesis system, the reaction mixture contains all the cellular components necessary to support protein synthesis including ribosomes, tRNA, rRNA, spermidine and physiological ions such as magnesium and potassium at appropriate concentrations and an appropriate pH. Reaction mixtures can be normally derived from a number of different sources including wheat germ, *E. coli* (S-30), red blood cells (reticulocyte lysate,) and oocytes, and once created can be stored as aliquots at about +4° C. to –70° C. The method of preparing such reaction mixtures is described by J. M. Pratt (*Transcription and Translation*, B. D. Hames and S. J. Higgins, Editors, p. 209, IRL Press, Oxford, 1984) which is hereby incorporated by reference Many different translation systems are commercially available from a number of manufacturers.

The misaminoacylated tRNA is added directly to the reaction mixture as a solution of predetermined volume and concentration. This can be done directly prior to storing the reaction mixture at –70° C. in which case the entire mixture is thawed prior to initiation of protein synthesis or prior to the initiation of protein synthesis. Efficient incorporation of markers into nascent proteins is sensitive to the final pH and magnesium ion concentration Reaction mixtures are normally about pH 6.8 and contain a magnesium ion concentration of about 3 mM. These conditions impart stability to the base-labile aminoacyl linkage of the misaminoacylated tRNA. Aminoacylated tRNAs are available in sufficient quantities from the translation extract. Misaminoacylated tRNAs charged with markers are added at between about 1.0 µg/ml to about 1.0 mg/ml, preferably at between about 10 µg/ml to about 500 µg/ml, and more preferably at about 150 µg/ml.

Initiation of protein synthesis occurs upon addition of a quantity of mRNA or DNA to the reaction mixture containing the misaminoacylated tRNAs. mRNA molecules may be prepared or obtained from recombinant sources, or purified from other cells by procedure such as poly-dT chromatography. One method of assuring that the proper ratio of the reaction mixture components is to use predetermined volumes that are stored in convenient containers such as vials or standard microcentrifuge tubes. For example, DNA and/or mRNA coding for the nascent proteins and the misaminoacylated tRNA solution are premixed in proper amounts and stored separately in tubes. Tubes are mixed when needed to initiate protein synthesis.

Translations in cell-free systems generally require incubation of the ingredients for a period of time. Incubation times range from about 5 minutes to many hours, but is preferably between about thirty minutes to about five hours and more preferably between about one to about three hours. Incubation may also be performed in a continuous manner whereby reagents are flowed into the system and nascent proteins removed or left to accumulate using a continuous flow system (A. S. Spirin et al., Sci. 242:1162–64, 1988). This process may be desirable for large scale production of nascent proteins. Incubation times vary significantly with the volume of the translation mix and the temperature of the incubation. Incubation temperatures can be between about 4° C. to about 60° C., and are preferably between about 15° C. to about 50° C., and more preferably between about 25° C. to about 45° C. and even more preferably at about 25° C. or about 37° C. Certain markers may be sensitive to temperature fluctuations and in such cases, it is preferable to conduct those incubations in the non-sensitive ranges. Translation mixes will typically comprise buffers such as Tris-HCl, Hepes or another suitable buffering agent to maintain the pH of the solution between about 6 to 8, and preferably at about 7. Again, certain markers may be pH sensitive and in such cases, it is preferable to conduct incubations outside of the sensitive ranges for the marker. Translation efficiency may not be optimal, but marker utility will be enhanced. Other reagents which may be in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process.

In cellular protein synthesis, it is necessary to introduce misaminoacylated tRNAs or markers into intact cells, cell organelles, cell envelopes and other discrete volumes bounded by an intact biological membrane, which contain a protein synthesizing system. This can be accomplished through a variety of methods that have been previously established such as sealing the tRNA solution into liposomes or vesicles which have the characteristic that they can be induced to fuse with cells. Fusion introduces the liposome or vesicle interior solution containing the tRNA into the cell. Alternatively, some cells will actively incorporate liposomes into their interior cytoplasm through phagocytosis. The tRNA solution could also be introduced through the process of cationic detergent mediated lipofection (Felgner et al., Proc. Natl. Acad. Sci. USA 84:7413–17, 1987), or injected into large cells such as oocytes. Injection may be through direct perfusion with micropipettes or through the method of electroporation.

Alternatively, cells can be permeabilized by incubation for a short period of time in a solution containing low concentrations of detergents in a hypotonic media. Useful detergents include Nonidet-P 40 (NP40), Triton X-100 (TX-100) or deoxycholate at concentrations of about 0.01 nM to 1.0 mM, preferably between about 0.1 µM to about 0.01 mM, and more preferably about 1 µM. Permeabilized cells allow marker to pass through cellular membranes unaltered and be incorporated into nascent proteins by host cell enzymes. Such systems can be formed from intact cells in culture such as bacterial cells, primary cells, immortalized cell lines, human cells or mixed cell populations. These cells may, for example, be transfected with an appropriate vector containing the gene of interest, under the control of a strong and possibly regulated promoter. Messages are expressed from these vectors and subsequently translated within cells. Intact misaminoacylated tRNA molecules, already charged with a non-radioactive marker could be introduced to cells and incorporated into translated product.

One example of the use of misaminoacylation to detect nascent protein is schematically represented in FIG. 4. A tRNA molecule is misaminoacylated with the marker which is highly fluorescent when excited with UV (ultraviolet) radiation. The misaminoacylated tRNA is then introduced into a cell-free protein synthesis extract and the nascent proteins containing the marker analog produced. Proteins in the cell-free extract are separated by polyacrylamide gel electrophoresis (PAGE). The resulting gel contains bands which correspond to all of the proteins present in the cell-free extract. The nascent protein is identified upon UV illumination of the gel by detection of fluorescence from the band corresponding to proteins containing marker. Detection can be through visible observation or by other conventional means of fluorescence detection.

The misaminoacylated tRNA can be formed by natural aminoacylation using cellular enzymes or misaminoacylation such as chemical misaminoacylation. One type of chemical misaminoacylation involves truncation of the tRNA molecule to permit attachment of the marker or marker precursor. For example, successive treatments with periodate plus lysine, pH 8.0, and alkaline phosphatase removes 3'-terminal residues of any tRNA molecule generating tRNA-OH-3' with a mononucleotide or dinucleotide deletion from the 3'-terminus (Neu and Heppel, J. Biol. Chem. 239:2927–34, 1964). Alternatively, tRNA molecules may be genetically manipulated to delete specific portions of the tRNA gene. The resulting gene is transcribed producing truncated tRNA molecules (Sampson and Uhlenbeck, Proc. Natl. Acad. Sci. USA 85:1033–37, 1988). Next, a dinucleotide is chemically linked to a modified amino acid or other marker by, for example, acylation. Using this procedure, markers can be synthesized and acylated to dinucleotides in high yield (Hudson, J. Org. Chem. 53:617–624, 1988; Happ et al., J. Org. Chem. 52:5387–91, 1987). These modified groups are bound together and linked via the dinucleotide to the truncated tRNA molecules in a process referred to as ligase coupling (FIG. 3B).

Figure 3B:
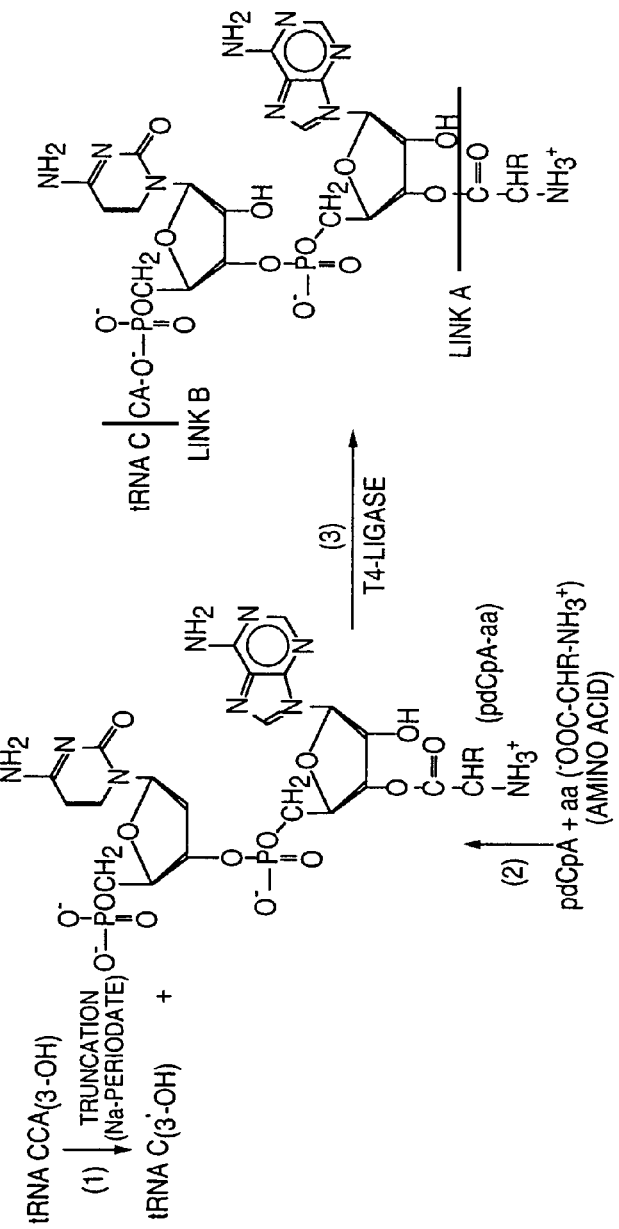

A different bond is involved in misaminoacylation (FIG. 3B, link B) than the bond involved with activation of tRNA by aminoacyl tRNA synthetase (FIG. 3B, link A). As T4 RNA ligase does not recognize the acyl substituent, tRNA molecules can be readily misaminoacylated with few chemical complications or side reactions (link B, FIG. 3B) (T. G. Heckler et al., Biochemistry 23:1468–73, 1984; and T. G. Heckler et al., Tetrahedron 40:87–94, 1984). This process is insensitive to the nature of the attached amino acid and allows for misaminoacylation using a variety of non-native amino acids. In contrast, purely enzymatic aminoacylation (link A) is highly sensitive and specific for the structures of substrate tRNA and amino acids.

Markers are basically molecules which will be recognized by the enzymes of the translation process and transferred from a charged tRNA into a growing peptide chain. To be useful markers must also possess certain physical and physio-chemical properties. Therefore, there are multiple criteria which can be used to identify a useful marker. First, a marker must be suitable for incorporation into a growing peptide chain. This may be determined by the presence of chemical groups which will participate in peptide bond formation. Second, markers should be attachable to a tRNA molecule. Attachment is a covalent interaction between the 3'-terminus of the tRNA molecule and the carboxy group of the marker or a linking group attached to the marker and to a truncated tRNA molecule. Linking groups may be nucleotides, short oligonucleotides or other similar molecules and are preferably dinucleotides and more preferably the dinucleotide CA. Third, markers should have one or more physical properties that facilitate detection and possibly isolation of nascent proteins. Useful physical properties include a characteristic electromagnetic spectral property such as emission or absorbance, magnetism, electron spin resonance, electrical capacitance, dielectric constant or electrical conductivity.

Useful markers are native amino acids coupled with a detectable label, detectable non-native amino acids, detectable amino acid analogs and detectable amino acid derivatives. Labels and other detectable moieties may be ferromagnetic, paramagnetic, diamagnetic, luminescent, electrochemiluminescent, fluorescent, phosphorescent or chromatic. Fluorescent moieties which are useful as markers include dansyl fluorophores, coumarins and coumarin derivatives, fluorescent acridinium moieties and benzopyrene based fluorophores. Preferably, the fluorescent marker has a high quantum yield of fluorescence at a wavelength different from native amino acids. Upon excitation at a preselected wavelength, the marker is detectable at low concentrations either visually or using conventional fluorescence detection methods. Electrochemiluminescent markers such as ruthenium chelates and its derivatives or nitroxide amino acids and their derivatives are preferred when extreme sensitivity is desired (J. DiCesare et al., BioTechniques 15:152–59, 1993). These markers are detectable at the fentomolar ranges and below.

In addition to fluorescent markers, a variety of other markers possessing specific physical properties can be used to detect nascent protein production. In general these properties are based on the interaction and response of the marker to electromagnetic fields and radiation and include absorption in the UV, visible and infrared regions of the electromagnetic spectrum presence of chromophores which are Raman active, and can be further enhanced by resonance Raman spectroscopy, electron spin resonance activity and nuclear magnetic resonances. These electromagnetic spectroscopic properties are preferably not possessed by native amino acids or are readily distinguishable from the properties of native amino acids. For example, the amino acid tryptophan absorbs near 290 nm, and has fluorescent emission near 340 nm when excited with light near 290 nm. Thus, tryptophan analogs with absorption and/or fluorescence properties that are sufficiently different from tryptophan can be used to facilitate their detection in proteins.

Many different modified amino acids which can be used as markers are commercially available (Sigma Chemical; St. Louis, Mo.; Molecular Probes; Eugene, Oreg.). One such marker is NE-dansyllysine created by the misaminoacylation of a dansyl fluorophore to a tRNA molecule (FIG. 5; scheme 1). The α-amino group of $N_\epsilon$-dansyllysine is first blocked with NVOC (ortho-nitro veratryl oxycarbonyl chloride) and the carboxyl group activated with cyanomethyl ester. Misaminoacylation is performed as described. The misaminoacylated tRNA molecules are then introduced into the protein synthesis system, whereupon the dansyllysine is incorporated directly into the newly synthesized proteins.

Another such marker is a fluorescent amino acid analog based on the highly fluorescent molecule coumarin (FIG. 5; scheme 2). This fluorophore has a much higher fluorescence quantum yield than dansyl chloride and can facilitate detection of much lower levels of nascent protein. In addition, this coumarin derivative has a structure similar to the native amino acid tryptophan. These structural similarities are useful where maintenance of the nascent proteins' native structure or function are important or desired. Coumarin is synthesized as depicted in FIG. 5 (scheme 2). Acetamidomalonate is alkylated with a slight excess of 4-bromomethyl coumarin (Aldrich Chemicals; Milwaukee; Wis.) in the presence of sodium ethoxide followed by acid hydrolysis. The corresponding amino acid as a hydrochloride salt that can be converted to the free amino acid analog.

The coumarin derivative can be used most advantageously if it misaminoacylates the tryptophan-tRNA, either enzymatically or chemically. When introduced in the form of the misaminoacylated tryptophan-tRNA, the coumarin amino acid will be incorporated only into tryptophan positions. By controlling the concentration of misaminoacylated tRNAs or free coumarin derivatives in the cell-free synthesis system, the number of coumarin amino acids incorporated into the nascent protein can also be controlled. This procedure can be utilized to control the amount of most any markers in nascent proteins.

Markers can be chemically synthesized from a native amino acid and a molecule with marker properties which cannot normally function as an amino acid. For example a highly fluorescent molecule can be chemically linked to a native amino acid group. The chemical modification occurs on the amino acid side-chain, leaving the carboxyl and amino functionalities free to participate in a polypeptide bond formation. Highly fluorescent dansyl chloride can be linked to the nucleophilic side chains of a variety of amino acids including lysine, arginine, tyrosine, cysteine, histidine, etc., mainly as a sulfonamide for amino groups or sulfate bonds to yield fluorescent derivatives. Such derivatization leaves the ability to form peptide bond intact, allowing the normal incorporation of dansyllysine into a protein.

A marker can also be modified after the tRNA molecule is aminoacylated or misaminoacylated using chemical reactions which specifically modify the marker without significantly altering the functional activity of the aminoacylated tRNA. These types of post-aminoacylation modifications may facilitate detection, isolation or purification, and can sometimes be used where the modification allow the nascent protein to attain a native or more functional configuration.

Fluorescent and other markers which have detectable electromagnetic spectral properties that can be detected by spectrometers and distinguished from the electromagnetic spectral properties on native amino acids. Spectrometers which are most useful include fluorescence, Raman, absorption, electron spin resonance, visible, infrared and ultraviolet spectrometers. Other markers, such as markers with distinct electrical properties can be detected by an apparatus such as an ammeter, voltmeter or other spectrometer. Physical properties of markers which relate to the distinctive interaction of the marker with an electromagnetic field is readily detectable using instruments such as fluorescence, Raman, absorption, electron spin resonance spectrometers. Markers may also undergo a chemical biochemical electrochemical or photochemical reaction such as a color change in response to external forces or agents such as an electromagnetic field or reactant molecules which allows its detection.

Normally detection first involves physical separation of the nascent proteins from other biomolecules present in the cellular or cell-free protein synthesis system. Protein separation can be performed using, for example, gel electrophoresis or column chromatography and can be further facilitated with affinity markers which uniquely bind acceptor groups. Detection of a marker containing a fluorophore by gel electrophoresis can be accomplished using conventional fluorescence detection methods.

After protein synthesis in a cell-free system, the reaction mixture, which contains all of the biomolecules necessary for protein synthesis as well as nascent proteins, is loaded onto a gel which may be composed of polyacrylamide or agarose (R. C. Allen et al., *Gel Electrophoresis and Isoelectric Focusing of Proteins*, Walter de Gruyter, New York 1984). This mixture also contains the misaminoacylated tRNAs bearing the marker as well as uncharged tRNAs. Subsequent to loading the reaction mixture, a voltage is applied which spatially separates the proteins on the gel in the direction of the applied electric field. The proteins separate and appear as a set of discrete or overlapping bands which can be visualized using a pre- or post-gel staining technique such as Coomasie blue staining. The migration of the protein band on the gel is a function of the molecular weight of the protein with increasing distance from the loading position being a function of decreasing molecular weight. Bands on the gel which contain nascent proteins will exhibit fluorescence when excited at a suitable wavelength. These bands can be detected visually, photographically or spectroscopically and, if desired, the nascent proteins purified from gel sections.

For example, if using dansyllysine as a marker, nascent proteins will fluoresce at 470 nm when excited by UV illumination. This fluorescence can be detected visually by simply using a standard hand-held UV illuminator or a transilluminator. Approximately 10 nanograms (ng) of the protein bacteriorhodopsin is detectable using this method. Also useful are electronic imaging devices which can rapidly screen and identify very low concentrations of markers.

The molecular weight and quantity of the nascent protein can be determined by comparison of its band-position on the gel with a set of bands of proteins of predetermined molecular weight. For example, a nascent protein of molecular weight 25,000 could be determined because of its relative position on the gel relative to a calibration gel containing the commercially available standard marker proteins of known quantities and with known molecular weights (bovine serum albumin, 66 kD; porcine heart fumarase, 48.5 kD; carbonic anhydrase, 29 kD, β-lactoglobulin, 18.4 kD; α-lactoglobulin, 14.2 kD; Sigma Chemical; St. Louis, Mo.).

Calibration proteins may also contain a similar markers for convenient detection using the same method as the gel bearing the nascent protein. This can be accomplished in many cases by directly reacting the calibration proteins with a molecule similar to the marker. For example, the calibration proteins can be modified with dansyl chloride so as to obtain their fluorescent derivatives (R. E. Stephens, Anal. Biochem. 65, 369–79, 1975). These fluorescent proteins can be analyzed using PAGE. Combined detection of these fluorescent calibration proteins along with that of nascent protein which contains fluorescent marker analog will accurately determine both the molecular weight and quantity of the nascent protein synthesized. If necessary, the amounts of marker within each calibration and nascent protein can be determined to provide an accurate quantitation.

Other methods of protein separation are also useful for detection and subsequent isolation and purification of nascent proteins containing markers. For example, proteins can be separated using capillary electrophoresis, isoelectric focusing, low pressure chromatography and high-performance or fast-pressure liquid chromatography (HPLC or FPLC). In these cases, the individual proteins are separated into fractions which can be individually analyzed by fluorescent detectors at the emission wavelengths of the markers. Alternatively, on-line fluorescence detection can be used to detect nascent proteins as they emerge from the column fractionation system. A graph of fluorescence as a function of retention time provides information on both the quantity and purity of nascent proteins produced.

Another embodiment of the invention is directed to a method for labeling, detecting and, if desired, isolating and purifying nascent proteins, as described above, containing cleavable markers. Cleavable markers comprise a chemical structure which is sensitive to external effects such as physical or enzymatic treatments, chemical or thermal treatments, electromagnetic radiation such as gamma rays, x-rays, ultraviolet light, visible light, infrared light, microwaves, radio waves or electric fields. The marker is aminoacylated to tRNA molecules as before using conventional technology or misaminoacylated and added to a translation system. After incubation and production of nascent proteins, marker can be cleaved by the application of specified treatments and nascent proteins detected. Alternatively, nascent proteins may also be detected and isolated by the presence or absence of the cleaved marker or the chemical moiety removed from the marker.

One example of a cleavable marker is a photocleavable marker such as chemical compounds which contain the 2-nitrobenzyl moiety (FIG. 6A). Upon illumination, these aromatic nitro compounds undergo an internal oxidation-reduction reaction (Pillai, Synthesis 1–26, 1980; Patchonik et al., J. Am. Chem. Soc. 92:6333–35, 1970). As a result, the nitro group is reduced to a nitroso group and an oxygen is inserted into the benzylic carbon-hydrogen bond at the ortho position. The primary photochemical process is the intramolecular hydrogen abstraction by the excited nitro group. This is followed by an electron-redistribution process to the aci-nitro form which rearranges to the nitroso product. Subsequent thermal reaction leads to the cleavage of substrate from the nitrobenzyl linkage.(FIG. 6B). Examples of other cleavable markers are shown in FIG. 7.

It may sometimes be desirable to create a distance between the substrate and the cleavable moiety. To accomplish this, cleavable moieties may be separated from substrates by cross-linker arms. Cross-Linkers increase substrate access and stabilize the chemical structure, and can be constructed using, for example, long alkyl chains or multiple repeat units of caproyl moieties linked via amide linkages.

Figure 8B:
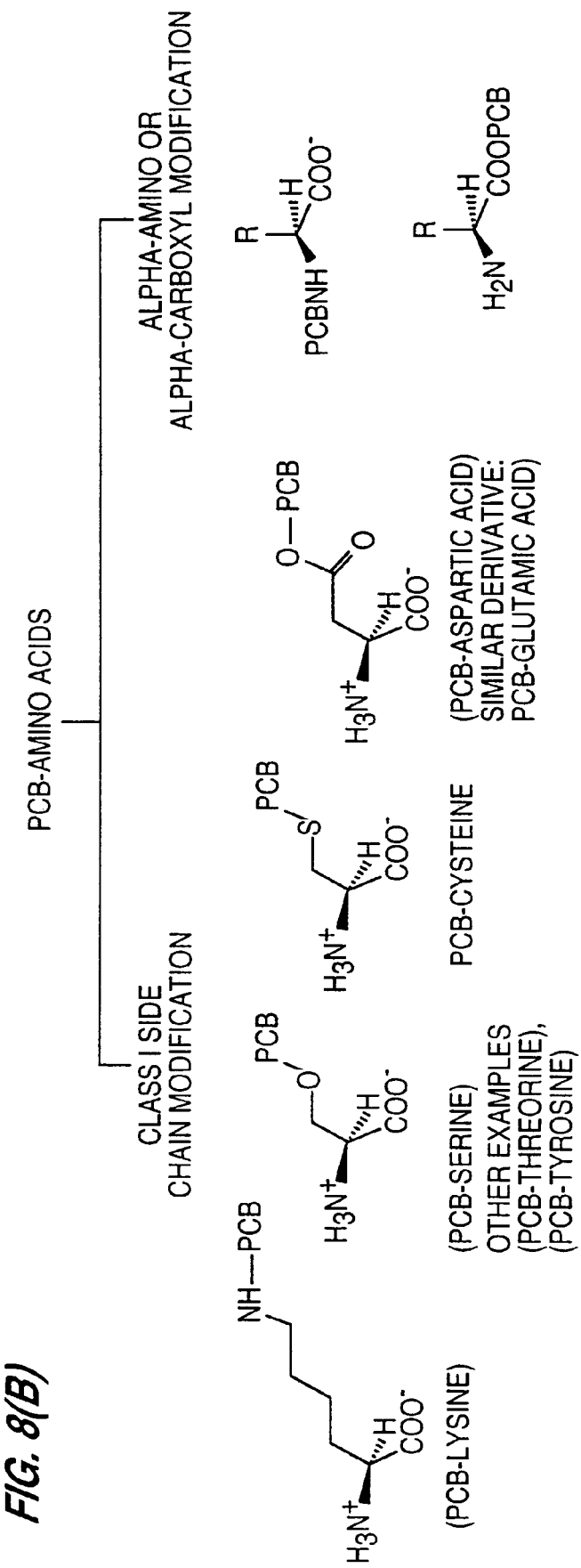

There are as many methods to synthesize cleavable markers as there are different markers. One example for the synthesis of photocleavable biotins based on nitrobenzyl alcohols involves four major steps. 2-bromo-2'-nitroacetphenone, a precursor of the photoreactive moiety, is first converted into an $\alpha$- or $\omega$-amino acid like $\epsilon$-aminocaprylic acid. The resulting acid and amino functionality of the photoreactive group is coupled using dicyclohexyl carbodiimide (DCC). The benzoyl carbonyl group of the resulting amide is reduced using sodium borohydride. The resulting derivative of nitrobenzyl alcohol is derivatized to obtain the final component which is able to react with biomolecular substrates, for example by the reaction with phosgene gas, to introduce the chloroformate functionality. The resulting compound is depicted in FIG. 8A along with alternative derivatives of PCB. Possible linkages to amino acids are depicted in FIG. 8B.

Cleavable markers can facilitate the isolation of nascent proteins. For example, one type of a cleavable marker is photocleavable biotin coupled to an amino acid. This marker can be incorporated into nascent proteins and the proteins purified by the specific interaction of biotin with avidin or streptavidin. Upon isolation and subsequent purification, the biotin is removed by application of electromagnetic radiation and nascent proteins utilized in useful applications without the complications of an attached biotin molecule. Other examples of cleavable markers include photocleavable coumarin, photocleavable dansyl, photocleavable dinitrophenyl and photocleavable coumarin-biotin. Photocleavable markers are cleaved by electromagnetic radiation such as UV light, peptidyl markers are cleaved by enzymatic treatments, and pyrenyl fluorophores linked by disulfide bonds are cleaved by exposure to certain chemical treatments such as thiol reagents.

Cleavage of photocleavable markers is dependent on the structure of the photoreactive moiety and the wavelength of electromagnetic radiation used for illumination. Other wavelengths of electromagnetic radiation should not damage the proteins or other chemical moieties. In the case of unsubstituted 2-nitrobenzyl derivatives, the yield of photolysis and recovery of the substrate are significantly decreased by the formation of side products which act as internal light filters and are capable to react with amino groups of the substrate. Typical illumination times vary from 1 to about 24 hours and yields are 1–95%. Radiation sources are placed within about 10 cm of the substrate proteins and set on low power so as to minimize side reactions, if any, which may occur in the nascent proteins. In the case of alpha-substituted 2-nitrobenzyl derivatives (methyl, phenyl, etc.), a considerable increase in rate of photo-removal as well as yield of the released substrate are observed. The introduction of other electron donor groups into phenyl rings of photoreactive moieties increases the yield of substrate. The general reaction for the photolysis of PCB is depicted in FIG. 9.

For enzymatic cleavage, markers introduced contain specific bonds which are sensitive to unique enzymes of chemical substances. Introduction of the enzyme or chemical into the protein mixture cleaves the marker from the nascent protein. When the marker is a modified amino acid, this can result in the production of native protein forms. Thermal treatments of, for example, heat sensitive chemical moieties operate in the same fashion Mild application of thermal energy, such as with microwaves or radiant heat, cleaves the sensitive marker from the protein without producing any significant damage to the nascent proteins.

Another embodiment of the invention is directed to a method for monitoring the synthesis of nascent proteins in a cellular or a cell-free protein synthesis system without separating the components of the system. These markers have the property that once incorporated into the nascent protein they are distinguishable from markers free in solution or linked to a tRNA This type of marker, also called a reporter, provides a means to detect and quantitate the synthesis of nascent proteins directly in the cellular or cell-free translation system.

Reporters have the characteristic that once incorporated into the nascent protein by the protein synthesizing system, they undergo a change in at least one of their physical or physiochemical properties. The resulting nascent protein can be uniquely detected inside the synthesis system without the need to separate or partially purify the protein synthesis system into its component parts. This type of marker provides a convenient non-radioactive method to monitor the production of nascent proteins without the necessity of first separating them from preexisting proteins in the protein synthesis system. A reporter marker would also provide a means to detect and distinguish between different nascent proteins produced at different times during protein synthesis by addition of markers whose properties are distinguishable from each other, at different times during protein expression. This would provide a means of studying differential gene expression.

One example of the utilization of reporters is schematically represented in FIG. 10. A tRNA molecule is misaminoacylated with a reporter (R) which has lower or no fluorescence at a particular wavelength for monitoring and excitation. The misaminoacylated tRNA is then introduced into a cellular or cell-free protein synthesis system and the nascent proteins containing the reporter analog are gradually produced. Upon incorporation of the reporter into the nascent protein (R*), it exhibits an increased fluorescence at known wavelengths. The gradual production of the nascent protein is monitored by detecting the increase of fluorescence at that specific wavelength.

The chemical synthesis of a reporter can be based on the linkage of a chemical moiety or a molecular component having reporter properties with a native amino acid residue. There are many fluorescent molecules which are sensitive to their environment and undergo a change in the wavelength of emitted light and yield of fluorescence. When these chemical moieties, coupled to amino acids, are incorporated into the synthesized protein, their environments are altered because of a difference between the bulk aqueous medium and the interior of a protein which can cause reduced accessibility to water, exposure to charged ionic groups, reduced mobility, and altered dielectric constant of the surrounding medium. Two such examples are shown in FIG. 11.

One example of a reporter molecule is based on a fluorescent acridinium moiety and has the unique property of altering its emission properties, depending upon polarity or viscosity of the microenvironment. It has a higher quantum yield of fluorescence when subjected to hydrophobic environment and/or viscosity. Due to the hydrophobicity of the reporter itself, it is more likely to be associated with the hydrophobic core of the nascent protein after incorporation into the growing nascent polypeptide. An increase in the fluorescence intensity is a direct measure of protein synthesis activity of the translation system. Although, the environment of each reporter residue in the protein will be different, and in some cases, the reporter may be present on the surface of the protein and exposed to an aqueous medium, a net change occurs in the overall spectroscopic properties of the reporters incorporated into the protein relative to bulk aqueous medium A change in the spectroscopic properties of only a subset of reporters in the protein will be sufficient to detect the synthesis of proteins that incorporate such reporters.

An alternative approach is to utilize a reporter which alters its fluorescent properties upon formation of a peptide bond and not necessarily in response to changes in its environment. Changes in the reporter's fluorescence as it partitions between different environments in the cell-free extract does not produce a large signal change compared to changes in fluorescence upon incorporation of the reporter into the nascent protein.

A second example of a reporter is a marker based on coumarin such as 6,7-(4', 5'-prolino)coumarin. This compound can be chemically synthesized by coupling a fluorophore like coumarin with an amino-acid structural element in such a way that the fluorophore would alter its emission or absorption properties after forming a peptide linkage (FIG. 11). For example, a proline ring containing secondary amino functions will participate in peptide bond formation similar to a normal primary amino group. Changes in fluorescence occur due to the co-planarity of the newly formed peptide group in relation to the existing fluorophore. This increases conjugation/delocalization due to the π-electrons of nitrogen-lone pair and carbonyl-group in the peptide bond. Synthesis of such compounds is based on coumarin synthesis using ethylacetoacetate (FIG. 11).

Reporters are not limited to those non-native amino acids which change their fluorescence properties when incorporated into a protein. These can also be synthesized from molecules that undergo a change in other electromagnetic or spectroscopic properties including changes in specific absorption bands in the UV, visible and infrared regions of the electromagnetic spectrum chromophores which are Raman active and can be enhanced by resonance Raman spectroscopy, electron spin resonance activity and nuclear magnetic resonances. In general, a reporter can be formed from molecular components which undergo a change in their interaction and response to electromagnetic fields and radiation after incorporation into the nascent protein.

Reporters may also undergo a change in at least one of their physical or physio-chemical properties due to their interaction with other markers which are incorporated into the same nascent protein. The interaction of two different markers with each other causes them to become specifically detectable. One type of interaction would be a resonant energy transfer which occurs when two markers are within a distance of between about 1 angstrom (Å) to about 50 Å, and preferably less than about 10 Å. In this case, excitation of one marker with electromagnetic radiation causes the second marker to emit electromagnetic radiation of a different wavelength which is detectable. A second type of interaction would be based on electron transfer between the two different markers which can only occur when the markers are less than about 5 Å. A third interaction would be a photochemical reaction between two markers which produces a new species that has detectable properties such as fluorescence. Although these markers are also present on the misaminoacylated tRNAs used for their incorporation into nascent proteins, the interaction of the markers occurs primarily when they are incorporated into protein due to their close proximity. In certain cases, the proximity of two markers in the protein can also be enhanced by choosing tRNA species that will insert markers into positions that are close to each other in either the primary, secondary or tertiary structure of the protein. For example, a tyrosine-tRNA and a tryptophan-tRNA could be used to enhance the probability for two different markers to be near each other in a protein sequence which contains the unique neighboring pair tyrosine-tryptophan.

As stated above, a principal advantage of using reporters is the ability to monitor the synthesis of proteins in cellular or a cell-free translation systems directly without further purification or isolation steps. Reporter markers may also be utilized in conjunction with cleavable markers that can remove the reporter property at will. Such techniques are not available using radioactive amino acids which require an isolation step to distinguish the incorporated marker from the unincorporated marker. With in vitro translation systems, this provides a means to determine the rate of synthesis of proteins and to optimize synthesis by altering the conditions of the reaction. For example, an in vitro translation system could be optimized for protein production by monitoring the rate of production of a specific calibration protein. It also provides a dependable and accurate method for studying gene regulation in a cellular or cell-free systems.

Another embodiment of the invention is directed to the use of markers that facilitate the detection or separation of nascent proteins produced in a cellular or cell-free protein synthesis system. Such markers are termed affinity markers and have the property that they selectively interact with molecules and/or materials containing acceptor groups. The affinity markers are linked by aminoacylation to tRNA molecules in an identical manner as other markers of non-native amino acid analogs and derivatives and reporter-type markers as described. These affinity markers are incorporated into nascent proteins once the misaminoacylated tRNAs are introduced into a translation system.

An affinity marker facilities the separation of nascent proteins because of its selective interaction with other molecules which may be biological or non-biological in origin through a coupling agent. For example, the specific molecule to which the affinity marker interacts, referred to as the acceptor molecule, could be a small organic molecule or chemical group such as a sulphydryl group (—SH) or a large biomolecule such as an antibody. The binding is normally chemical in nature and may involve the formation of covalent or non-covalent bonds or interactions such as ionic or hydrogen bonding. The binding molecule or moiety might be free in solution or itself bound to a surface, a polymer matrix, or a reside on the surface of a substrate. The interaction may also be triggered by an external agent such as Light, temperature, pressure or the addition of a chemical or biological molecule which acts as a catalyst.

The detection and/or separation of the nascent protein and other preexisting proteins in the reaction mixture occurs because of the interaction, normally a type of binding, between the affinity marker and the acceptor molecule. Although, in some cases some incorporated affinity marker will be buried inside the interior of the nascent protein, the interaction between the affinity marker and the acceptor molecule will still occur as long as some affinity markers are exposed on the surface of the nascent protein. This is not normally a problem because the affinity marker is distributed over several locations in the protein sequence.

Affinity markers include native amino acids, non-native amino acids, amino acid derivatives or amino acid analogs in which a coupling agent is attached or incorporated. Attachment of the coupling agent to, for example, a non-native amino acid may occur through covalent interactions, although non-covalent interactions such as hydrophilic or hydrophobic interactions, hydrogen bonds, electrostatic interactions or a combination of these forces are also possible. Examples of useful coupling agents include molecules such as haptens, immunogenic molecules, biotin and biotin derivatives, and fragments and combinations of these molecules. Coupling agents enable the selective binding or attachment of newly formed nascent proteins to facilitate their detection or isolation. Coupling agents may contain antigenic sites for a specific antibody, or comprise molecules such as biotin which is known to have strong binding to acceptor groups such as streptavidin. For example, biotin may be covalently linked to an amino acid which is incorporated into a protein chain. The presence of the biotin will selectively bind only nascent proteins which incorporated such markers to avidin molecules coated onto a surface. Suitable surfaces include resins for chromatographic separation, plastics such as tissue culture surfaces for binding plates, microtiter dishes and beads, ceramics and glasses, particles including magnetic particles, polymers and other matrices. The treated surface is washed with, for example, phosphate buffered saline (PBS), to remove non-nascent proteins and other translation reagents and the nascent proteins isolated. In some case these materials may be part of biomolecular sensing devices such as optical fibers, chemfets, and plasmon detectors.

One example of an affinity marker is dansyllysine (FIG. 5). Antibodies which interact with the dansyl ring are commercially available (Sigma Chemical; St. Louis, Mo.) or can be prepared using known protocols such as described in *Antibodies: A Laboratory Manual* (E. Harlow and D. Lane, editors, Cold Spring Harbor Laboratory Press, 1988) which is hereby specifically incorporated by reference. Many conventional techniques exist which would enable proteins containing the dansyl moiety to be separated from other proteins on the basis of a specific antibody-dansyl interaction. For example, the antibody could be immobilized onto the packing material of a chromatographic column. This method, known as affinity column chromatography, accomplishes protein separation by causing the target protein to be retained on the column due to its interaction with the immobilized antibody, while other proteins pass through the column. The target protein is then released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.).

Separation can also be performed through an antibody-dansyl interaction using other biochemical separation methods such as immunoprecipitation and immobilization of the antibodies on filters or other surfaces such as beads, plates or resins. For example, protein could be isolated by coating magnetic beads with a protein-specific antibody. Beads are separated from the extract using magnetic fields. A specific advantage-of using dansyllysine as an affinity marker is that once a protein is separated it can also be conveniently detected because of its fluorescent properties.

In addition to antibodies, other biological molecules exist which exhibit equally strong interaction with target molecules or chemical moieties. An example is the interaction of biotin and avidin. In this case, an affinity analog which contains the biotin moiety would be incorporated into the protein using the methods which are part of the present invention. Biotin-lysine amino acid analogs are commercially available (Molecular Probes; Eugene, Oreg.).

Affinity markers can also comprise cleavable markers incorporating a coupling agent. This property is important in cases where removal of the coupled agent is required to preserve the native structure and function of the protein and to release nascent protein from acceptor groups. In some cases, cleavage and removal of the coupling agent results in production of a native amino acid. One such example is photocleavable biotin coupled to an amino acid.

Photocleavable biotin contains a photoreactive moiety which comprises a phenyl ring derivatized with functionalities represented in FIG. 12 by X, Y and Z. X allows linkage of PCB to the bimolecular substrate through the reactive group X'. Examples of X' include Cl, O-N-hydroxysuccinimidyl, $OCH_2CN$, $OPhF_5$, $OPhCl_5$, $N_3$. Y represents a substitution pattern of a phenyl ring containing one or more substitutions such as nitro or alkoxyl. The functionality Z represents a group that allows linkage of the cross-linker moiety to the photoreactive moiety. The photoreactive moiety has the property that upon illumination, it undergoes a photoreaction that results in cleavage of the PCB molecule from the substrate.

A lysine-tRNA is misaminoacylated with photocleavable biotin-lysine, or chemically modified to attach a photocleavable biotin amino acid. The misaminoacylated tRNA is introduced into a cell-free protein synthesizing system and nascent proteins produced. The nascent proteins can be separated from other components of the system by streptavidin-coated magnetic beads using conventional methods which rely on the interaction of beads with a magnetic field. Nascent proteins are released then from beads by irradiation with UV light of approximately 280 nm wavelength.

Many devices designed to detect proteins are based on the interaction of a target protein with specific immobilized acceptor molecule. Such devices can also be used to detect nascent proteins once they contain affinity markers such as biodetectors based on sensing changes in surface plasmons, light scattering and electronic properties of materials that are altered due to the interaction of the target molecule with the immobilized acceptor group.

Nascent proteins, including those which do not contain affinity-type markers, may be isolated by more conventional isolation techniques. Some of the more useful isolation techniques which can be applied or combined to isolate and purify nascent proteins include chemical extraction, such as phenol or chloroform extract, dialysis, precipitation such as ammonium sulfate cuts, electrophoresis, and chromatographic techniques. Chemical isolation techniques generally do not provide specific isolation of individual proteins, but are useful for removal of bulk quantities of non-proteinaceous material. Electrophoretic separation involves placing the translation mixture containing nascent proteins into wells of a gel which may be a denaturing or non-denaturing polyacrylamide or agarose gel. Direct or pulsed current is applied to the gel and the various components of the system separate according to molecular size, configuration, charge or a combination of their physical properties. Once distinguished on the gel, the portion containing the isolated proteins removed and the nascent proteins purified from the gel. Methods for the purification of protein from acrylamide and agarose gels are known and commercially available.

Chromatographic techniques which are useful for the isolation and purification of proteins include gel filtration, fast-pressure or high-pressure liquid chromatography, reverse-phase chromatography, affinity chromatography and ion exchange chromatography. These techniques are very useful for isolation and purification of proteins species containing selected markers.

Another embodiment of the invention is directed to the incorporation of non-native amino acids or amino acid derivatives with marker or affinity properties at the amino-terminal residue of a nascent protein (FIG. 13). This can be accomplished by using the side chain of an amino acid or by derivatizing the terminal amino group of an amino acid. In either case the resulting molecule is termed an amino acid derivative. The amino-terminal residue of a protein is free and its derivatization would not interfere with formation of the nascent polypeptide. The non-native amino acid or amino acid derivative is then used to misaminoacylate an initiator tRNA which only recognizes the first AUG codon signaling the initiation of protein synthesis. After introduction of this misaminoacylated initiator tRNA into a protein synthesis system, marker is incorporated only at the amino terminal of the nascent protein. The ability to incorporate at the N-terminal residue can be important as these nascent molecules are most likely to fold into native conformation. This can be useful in studies where detection or isolation of functional nascent proteins is desired.

It may often be advantageous to incorporate more than one marker into a single species of protein. This can be accomplished by using a single tRNA species such as a lysine tRNA misaminoacylated with both a marker such as dansyllysine and a coupling agent such as biotin-lysine. Alternatively, different tRNAs which are each misaminoacylated with different markers can also be utilized. For example, the coumarin derivative could be used to misaminoacylate a tryptophan tRNA and a dansyllysine used to misaminoacylate a lysine tRNA.

One use of multiple misaminoacylated tRNAs is to study the expression of proteins under the control of different genetic elements such as repressors or activators, or promoters or operators. For example, the synthesis of proteins at two different times in response to an internal or external agent could be distinguished by introducing misaminoacylated tRNAs at different times into the cellular or cell-free protein synthesis system A tRNA$^{tyr}$ might be charged with marker A and a tRNA$^{lys}$ charged with marker B, yielding A-tRNA$^{tyr}$ and B-tRNA$^{lys}$, respectively. In this case, protein one under the control of one promoter can be labeled by adding the A-tRNA$^{tyr}$ to the reaction system If a second misaminoacylated tRNA, B-tRNA$^{lys}$ is then added and a second promoter for protein two activated, the nascent protein produced will contain both label A and B. Additional markers could also be added using additional tRNA molecules to further study the expression of additional proteins. The detection and analysis of multiply labeled nascent proteins can be facilitated by using the multicolored electrophoresis pattern reading system, described in U.S. Pat. No. 5,190,632, which is specifically incorporated by reference, or other multi-label reading systems such as those described in U.S. Pat. Nos. 5,069,769 and 5,137,609, which are both hereby specifically incorporated by reference.

A second use of multiple misaminoacylated tRNAs is in the combined isolation and detection of nascent proteins. For example, biotin-lysine marker could be used to misaminoacylate one tRNA and a coumarin marker used to misaminoacylate a different tRNA. Magnetic particles coated with streptavidin which binds the incorporated lysine-biotin would be used to isolate nascent proteins from the reaction mixture and the coumarin marker used for detection and quantitation.

A schematic diagram of the basics of the above methods is shown in FIG. 14. In a first step, the marker selected (M), which may have reporter (R) or affinity (A) properties, is chemically or enzymatically misaminoacylated to a single tRNA species or a mixture of different tRNAs. Prior to protein synthesis, a predetermined amount of the misaminoacylated tRNA, charged with the fluorescent marker is mixed with the cell-free protein synthesis reaction system at concentrations sufficient to allow the misaminoacylated tRNA to compete effectively with the corresponding tRNA. After an incubation of about 1–3 hours, the reaction mixture is analyzed using conventional polyacrylamide or agarose gel electrophoresis. After electrophoresis, the gel is illuminated by UV radiation. Bands due to the nascent protein exhibit distinct fluorescence and can be easily and rapidly distinguished, either visually or photographically, from non-fluorescent bands of preexisting proteins. Nascent proteins can be isolated by excising the fluorescent band and electroeluting the protein from the extracted gel pieces. The quantities and molecular weights of the nascent proteins can be determined by comparison of its fluorescence with the fluorescence produced by a set of proteins with known molecular weights and known quantities. The results of the assay can be recorded and stored for further analysis using standard electronic imaging and photographic or spectroscopic methods.

Another embodiment of the invention is directed to a composition comprising nascent proteins isolated or purified by conventional methods after translation in the presence of markers. Compositions can be utilized in manufacturing for the preparation of reagents such as coatings for tissue culture products and in the pharmaceutical industry.

Incorporation of markers into nascent proteins utilized in manufacturing facilitates analysis of the final manufactured product or process by detection of marker. For example, nascent proteins produced may be used as coatings for tissue culture products. The reproducibility of a particular coating process could be accurately determined by detecting variations of marker emissions over the surface of the coated product. In addition, non-toxic markers incorporated into proteins encompassed within a pharmaceutical preparation such as a hormone, steroid, immune product or cytokine can be utilized to facilitate safe and economical isolation of that protein preparation. Such products could be used directly without the need for removal of marker. When very low concentrations of marker are preferred, limiting amounts of marked proteins could be used to follow a protein through a purification procedure. Such proteins can be efficiently purified and the purity of the resulting composition accurately determined. In addition, the presence of markers may facilitate study and analysis of pharmaceutical compositions in testing. For example, markers can be utilized to determine serum half-life, optimum serum levels and the presence or absence of break-down products of the composition in a patient.

Alternatively, nascent proteins may contain specific markers which serve as therapeutically useful compounds such as toxic substances. These proteins are administered to a patient and the therapeutic moiety released after proteins have identified and possibly bound to their respective targets. Release may be electrical stimulation, photochemical cleavage or other means whereby the moiety is specifically deposited in the area targeted by the nascent proteins. In addition, moieties such as modified toxins may be utilized which become toxic only after release from nascent proteins. Nascent protein may also serve as a pharmaceutical carrier which bestows the incorporated marker with active therapeutic function or prevents marker from breaking down in the body prior to its therapeutic or imaging action.

The incorporation of cleavable markers in nascent proteins further provides a means for removal of the non-native portion of the marker to facilitate isolation of the protein in a completely native form. For example, a cleavable affinity marker such as photocleavable biotin introduced into a nascent protein facilitates economical isolation of the protein and allows for the removal of the marker for further use as a pharmaceutical composition.

Pharmaceutical compositions of proteins prepared by translation in the presence of markers may further comprise a pharmaceutically acceptable carrier such as, for example, water, oils, lipids, polysaccharides, glycerols, collagens or combinations of these carriers. Useful immunological compositions include immunologically active compositions, such as a vaccine, and pharmaceutically active compositions, such as a therapeutic or prophylactic drug which can be used for the treatment of a disease or disorder in a human.

Another embodiment of the invention is directed to diagnostic kits or aids containing, preferably, a cell-free translation containing specific misaminoacylated tRNAs which incorporate markers into nascent proteins coded for by mRNA or genes, requiring coupled transcription-translation systems, and are only detectably present in diseased biological samples. Such kits may be useful as a rapid means to screen humans or other animals for the presence of certain diseases or disorders. Diseases which may be detected include infections, neoplasias and genetic disorders. Biological samples most easily tested include samples of blood, serum, tissue, urine or stool, nasal cells or spinal fluid. In one example, misaminoacylate fmet-tRNAs could be used as a means to detect the presence of bacteria in biological samples containing prokaryotic cells. Kits would contain translation reagents necessary to synthesize protein plus tRNA molecules charged with detectable non-radioactive markers. The addition of a biological sample containing the bacteria-specific genes would supply the nucleic acid needed for translation Bacteria from these samples would be selectively lysed using a bacteria directed toxin such as Colicin E1 or some other bacteria-specific permeabilizing agent. Specific genes from bacterial DNA could also be amplified using specific oligonucleotide primers in conjunction with polymerase chain reaction (PCR), as described in U.S. Pat. No. 4,683,195, which is hereby specifically incorporated by reference. Nascent proteins containing marker would necessarily have been produced from bacteria. Utilizing additional markers or additional types of detection kits, the specific bacterial infection may be identified.

Kits may also be used to detect specific diseases such as familial adenomatous polyposis. In about 30 to 60% of cases of familial adenomatous polyposis, the diseased tissues also contain chain terminated or truncated transcripts of the APC gene (S. M. Powell et al., N. Engl. J. Med. 329:1982–87, 1993). Chain termination occurs when frameshift cause a stop codon such as UAG, UAA or UGA to appear in the reading frame which terminates translation. Using misaminoacylated tRNAs which code for suppressor tRNAs, such transcripts can be rapidly and directly detected in inexpensive kits. These kits would contain a translation system, charged suppressor tRNAs containing detectable markers, for example photocleavable coumarin-biotin, and appropriate buffers and reagents. A biological sample, such as diseased cells, tissue or isolated DNA or mRNA, is added to the system, the system is incubated and the products analyzed. Analysis and, if desired, isolation is facilitated by a marker such as photocleavable coumarin-biotin which can be specifically detected using streptavidin coupled to magnetic beads. Such kits would provide a rapid, sensitive and selective non-radioactive diagnostic assay for the presence or absence of the disease.

A variety of proteins and protein derivatives useful in the treatment of human diseases can be produced in a cell-free system. This includes toxins which are difficult to grow in cellular systems because of the toxicity to the cell, proteins involved in gene regulation, transcription, translation and cell-division. Examples include cis-A and rel which are difficult to express and produce in cellular systems due to interference with the native mechanisms of the cell, and proteins modified with non-native amino acids for labeling of or localization in specific human cells, or for interaction with other biomolecules of a cell. One example is the protein coded for the gene MTS1 which may be missing or defective in more that 50% of all human cancer cells. These nascent proteins can be conveniently isolated from the cell-free synthesis system by incorporation of detectable markers. For example, a methionine initiator tRNA can be misaminoacylated with a photocleavable biotin amino acid or photocleavable coumarin-biotin amino acid which is introduced into the cell-free synthesis system along with the plasmids containing the gene that codes for the desired protein product. The nascent protein is isolated from the cell-free reaction mixture by the introduction of streptavidin coated magnetic beads. Irradiation with light at between about 250 nm to about 350 nm, preferably between about 280 nm to about 320 nm, and more preferably at about 300 nm, causes the cleavage of the bonds between photocleavable biotin and the coumarin amino acid.

Nascent proteins with defined therapeutic properties can be introduced to a patient such as a human as a preparation combined with a pharmaceutically acceptable carrier. In some cases, marker may serve to couple the nascent protein to a pharmaceutically acceptable carrier. For example, streptavidin immobilized on a biodegradable magnetic bead carrier (K. J. Widder et al, Proc. Soc. Exp. Biol. & Med. 58:141–46, 1978) such as the MicroImageETM beads offered commercially by the OmniQuest corporation can be used to bind a nascent protein incorporating the marker photocleavable biotin. In the case of a biodegradable magnetic beads, composed of albumin, the nascent protein is isolated from the reaction mixture as described above using such bead coated with streptavidin. It is then introduced intra-arterially and caused to concentrate at a tumor site by application of an external magnetic field with an external magnet or internal application of a magnetic field through surgical implantation of a small magnet. Once the magnetic bead carrier is concentrated, the therapeutic or marker protein is released by the action of light which cleaves the photocleavable biotin that binds the nascent protein to the magnetic beads or alternatively through degradation of the bead which may be enhanced through other mechanisms.

A nascent protein may contain a non-radioactive marker which is used to determine the site of a tumor, pathogen or other abnormal tissues in the body. One example of a marker protein would be a nascent protein that includes a non-radioactive marker which acts as an MRI image enhancer. A second would be a nascent protein which contains a fluorescent marker such as coumarin or photocleavable coumarin. The nascent protein may be chosen to have a high affinity to specific antigens that reside on the tumor cells, pathogenic virus or bacteria. The non-radioactive marker may also be used to monitor the half-life of the nascent protein. For example, a specific fluorescence signal from a reporter marker may be monitored to determine the rate of proteolytic degradation of a particular protein in the body.

Nascent proteins containing markers are also useful to enhance or replace presently available protein products. One example involves bacteriorhodopsin, which has photochemical properties including a rapid change in its visible absorption spectrum and has been utilized in a variety of opto-electronic devices including spatial light modulators, real-time holographic interferometers, and photodetectors (D. Oesterhelt et al., Quart. Rev. Biophys. 4:425–78, 1991). The incorporation of fluorescent markers enhance the usefulness of bacteriorhodopsin in these devices by providing a means of determining the state of bacteriorhodopsin through fluorescent emission. Further, bacteriorhodopsin can also be created with a photocleavable biotin moiety. These markers are incorporated into proteins by misaminoacylation. After isolation, the modified bacteriorhodopsin can be reconstituted in halobacterial lipids (S. Sonar et al., Biochem. 32:13777–81, 1993) and incorporated into thin films by a process for producing a molecular oriented film such as described in U.S. Pat. No. 4,241,0050, which is hereby specifically incorporated by reference. These thin films can be utilized in a variety of opto-electronic devices such as in a spatial light modulator.

In a second example, PCB modified bacteriorhodopsin can be reconstituted into two-dimensional self-assembling arrays which are used as a template for producing a patterned overlayer such as described in U.S. Pat. Nos. 4,728,591 and 4,802,951, which are hereby specifically incorporated by reference. This overlayer could consist of enzymes or other biomolecules which selectively interact with the affinity marker and assemble into a pattern that replicates the bacteriorhodopsin template pattern. Additional patterning could be accomplished by selectively irradiating specific areas with light causing release of the overlying enzymes or by using a near field scanning optical microscope. Patterning of enzymes at the nanometer level can be used in the production of molecular devices.

The following examples illustrate embodiments of the invention, but should not be viewed as limiting the scope of the invention.

EXAMPLES

Example 1

Preparation of Markers.

Synthesis of Coumarin Amino Acid: 4-(Bromomethyl)-7-methoxy coumarin (FIG. 15, compound 1; 6.18 mmole) and diethylacetamidomalonate (FIG. 15, compound 2; 6.18 mmole) were added to a solution of sodium ethoxide in absolute ethanol and the mixture refluxed for 4 hours. The intermediate obtained (FIG. 15, compound 3) after neutralization of the reaction mixture and chloroform extraction was further purified by crystallization from methanolic solution. This intermediate was dissolved in a mixture of acetone and HCl (1:1) and refluxed for one hour. The reaction mixture was evaporated to dryness, and the amino acid hydrochloride precipitated using acetone. This hydrochloride was converted to free amino acid (FIG. 15, compound 4) by dissolving in 50% ethanol and adding pyridine to pH 4–5. The proton ($^1$H) NMR spectrum of the free amino acid was as follows: (m.p. 274–276° C., decomp.) —OCH$_3$ ($\delta$ 3.85 s, 3H), —CH$_2$— ($\delta$ 3.5 d, 2H), $\alpha$-CH— ($\delta$ 2.9 t, 1H),CH—CO ($\delta$ 6.25 s, 1H), ring H ($\delta$ 7.05 s, 1H), ($\delta$ 7.8 d, 2H).

Synthesis of Fmoc derivative of coumarin: Coumarin amino acid (1.14 mmol) was reacted with Fluorenylmethyloxycarbonyl N-hydroxysuccininmidyl ester (Fmoc-NHS ester) 1.08 mmol) in the presence of 1.14 mmol of triethylamine for 30 minutes at room temperature. The reaction mixture was acidified and the precipitate washed with 1 N HCl and dried. The NMR spectrum of the free amino acid was as follows: (MP 223–225° C.) —OCH$_3$ ($\delta$ 3.85 s, 3H), —CH$_2$Br ($\delta$ 3.5 broad singlet, 2H), $\alpha$-CH—($\delta$ 3.0 t, 1H), CH—CO ($\delta$ 6.22 m, 1H), ring H ($\delta$ 7.05 s, 1H), ($\delta$ 7.8 d, 2H), fluorene H CH$_2$—CH ($\delta$ 4.2 m, 2H), CH$_2$—CH ($\delta$ 4.25 m, 1H), aromatic regions showed characteristic multiplets.

Synthesis of PCB: Photocleavable biotin was synthesized as described below. 2-bromo, 2'-nitroacetophenone (FIG. 15, compound 5) was converted first into its hexamethyltetraamommonium salt which was decomposed to obtain 2-amino, 2'-nitroacetophenone (FIG. 15, compound 6). Biotin N-hydroxysuccinimidyl ester (FIG. 15, compound 7; Sigma Chemical; St. Louis, Mo.) was reacted with a 6-aminocaproic acid (FIG. 15, compound 8) to obtain the corresponding acid (FIG. 15, compound 9). This acid was coupled with the 2-amino, 2'nitroacetophenone using DCC to obtain the ketone (FIG. 15, compound 10). The ketone was reduced using sodium borohydride to obtain the alcohol (FIG. 15, compound 11) which was further converted into its chloroformate derivative (FIG. 15, compound 12). The proton NMR spectrum of the derivative (compound 12) was as follows: (δ 13 m, 3H), (δ 1.4 m, 2H), (δ 1.5 m, 5H) (δ 1.62 m, 1H), (δ 2.1 t, 2H) (δ 2.4 t, 2H), (δ 2.6 d, 1H), (δ 2.8 m, 1H), (δ 3.0 t, 1H), (δ 3.1 m 1H), (δ 4.15 qt, 1H) (δ 4.42 qt, 1H), (δ 5.8 t, 1H), (δ 6.25 s, 1H), (δ 6.45 s, 1H), (δ 75 t, 1H), (δ 7.75 m, 4H), (δ 7.9 d, 1H).

Example 2

Misaminoacylation of tRNA.

The general strategy used for generating misaminoacylated tRNA is shown in FIG. 16 and involved truncation of tRNA molecules, dinucleotide synthesis (FIG. 17), aminoacylation of the dinucleotide (FIG. 18) and ligase mediated coupling.

a) Truncated tRNA molecules were generated by periodate degradation in the presence of lysine and alkaline phosphatase basically as described by Neu and Heppel (J. Biol. Chem. 239:2927–34, 1964). Briefly, 4 mmoles of uncharged E. coli tRNA$^{Lys}$ molecules (Sigma Chemical; St. Louis, Mo.) were truncated with two successive treatments of 50 mM sodium metaperiodate and 0.5 M lysine, pH 9.0, at 60° C. for 30 minutes in a total volume of 50 µl. Reaction conditions were always above 50° C. and utilized a 10-fold excess of metaperiodate. Excess periodate was destroyed treatment with 5 µl of 1M glycerol. The pH of the solution was adjusted to 8.5 by adding 15 µl of Tris-HCl to a final concentration of 0.1 M. The reaction volume was increased to 150 µl by adding 100 µl of water. Alkaline phosphatase (15 µl, 30 units) was added and the reaction mixture incubated again at 60° C. for two hours. Incubation was followed by ethanol precipitation of total tRNA, ethanol washing, drying the pellet and dissolving the pellet in 20 µl water. This process was repeated twice to obtain the truncated tRNA.

b) Dinucleotide synthesis was carried out basically as performed by Hudson (J. Org. Chem. 53:617–24, 1988), and can be described as a three step process, deoxycytidine protection, adenosine protection and dinucleotide synthesis.

Deoxycytidine protection: All reaction were conducted at room temperature unless otherwise indicated. First, the 5' and 3' hydroxyl groups of deoxycytidine were protected by reacting with 4.1 equivalents of trimethylsilyl chloride for 2 hours with constant stirring. Exocyclic amine function was protected by reacting it with 1.1 equivalents of Fmoc-Cl for 3 hours. Deprotection of the 5' and 3' hydroxyl was accomplished by the addition of 0.05 equivalents of KF and incubation for 30 minutes. The resulting product (FIG. 17, compound 19) was produced at an 87% yield. Phosphate groups were added by incubating this compound with 1 equivalent of bis-(2-chlorophenyl)phosphorochloridate and incubating the mixture for 2 hours at 0° C. The yield in this case was 25–30%.

Adenosine protection: Trimethylsilyl chloride (4.1 equivalents) was added to adenosine residue and incubated for 2 hours, after which, 1.1 equivalents of Fmoc-Cl introduced and incubation continued for 3 hours. The TMS groups were deprotected with 0.5 equivalents of fluoride ions as described above. The Fmoc protected adenosine, (compound 22) was obtained in a 56% yield. To further protect the 2'-hydroxyl, compound 22 was reacted with 1.1 equivalents of tetraisopropyl disiloxyl chloride (TIPDSCl$_2$) for 3 hours which produces compound 23 at a 68–70% yield. The compound was converted to compound 24 by incubation with 20 equivalents of dihydropyran and 0.33 equivalents of p-toluenesulfonic add in dioxane for about 4–5 hours. This compound was directly converted without isolation into compound 25 (FIG. 17) by the addition of 8 equivalents of tetrabutyl ammonium fluoride in a mixture of tetrahydrofuran, pyridine and water.

Dinucleotide synthesis: The protected deoxycytidine, compound 20, and the protected adenosine, compound 25 (FIG. 17), were coupled by the addition of 1.1 equivalents of 2-chlorophenyl bis-(1-hydroxy benzotriazolyl) phosphate in tetrahydrofuran with constant stirring for 30 minutes. This was followed by the addition of 1.3 equivalents of protected adenosine, compound 25, in the presence of N-methylimidazole for 30 minutes. The coupling yield was about 70% and the proton NMR spectrum of the coupled product, compound 26 (FIG. 17), was as follows: (δ 8.76 m, 2H), (δ 8.0 m, 3H), (δ 7.8 m, 3H) (δ 7.6 m, 4H), (δ 7.5 m, 3H), (δ 7.4 m, 18H), (δ 7.0 m, 2H), (δ 4.85 m, 14H), (δ 4.25 m, 1H); (δ 3.6 m, 2H), (δ 3.2 m, 2H) (δ 2.9 m, 3H), (δ 2.6 m, 1H), (δ 2.0–1.2 m, 7H).

c) Aminoacylation of the dinucleotide was accomplished by linking the protected marker amino acid, Fmoc-coumarin, to the dinucleotide with an ester linkage. First, the protected amino add was activated with 6 equivalents of benzotriazol-1-yl-oxy tris-(dimethylamino) phosphonium hexafluoro phosphate and 60 equivalents of 1-hydroxybenzotriazole in tetrahydrofuran. The mixture was incubated for 20 minutes with continuous stirring. This was followed with the addition of 1 equivalent of dinucleotide in 3 equivalents N-methylimidazole, and the reaction continued at room temperature for 2 hours. Deprotection was carried out by the addition of tetramethyl guanidine and 4-nitrobenzaldoxime, and continuous stirring for another 3 hours. The reaction was completed by the addition of acetic acid and incubation, again with continuous stirring for 30 minutes at 0° C. which produced the aminoacylated dinucleotide (FIG. 18).

d) Ligation of the tRNA to the aminoacylated dinucleotide was performed basically as described by T. G. Heckler et al. (Tetrahedron 40: 87–94, 1984). Briefly, truncated tRNA molecules (8.6 O.D.$_{260}$ units/ml) and aminoacylated dinucleotides (4.6 O.D.$_{260}$ units/ml), were incubated with 340 units/ml T4 RNA ligase for 16 hours at 4° C. The reaction buffer included 55 mM Na-Hepes, pH 7.5, 15 mM MgCl$_2$, 250 µM ATP, 20 µg/ml BSA and 10% DMSO. After incubation, the reaction mixture was diluted to a final concentration of 50 mM NaOAc, pH 4.5, containing 10 mM MgCl$_2$. The resulting mixture was applied to a DEAE-cellulose column (1 ml), equilibrated with 50 mM NaOAc, pH 4.5, 10 mM, MgCl$_2$, at 4° C. The column was washed with 0.25 mM NaCl to remove RNA ligase and other non-tRNA components. The tRNA-containing factions were pooled and loaded onto a BD-cellulose column at 4° C., that had been equilibrated with 50 mM NaOAc, pH 4.5, 10 mM MgCl$_2$, and 1.0 M NaCl. Unreacted tRNA was removed by washes with 10 ml of the same buffer. Pure misaminoacylated tRNA was obtained by eluting the column with buffer containing 25% ethanol.

Example 3

Preparation of Extract and Template for Cell-Free Translation.

Preparation of extract: Wheat germ embryo extract was prepared by floatation of wheat germs to enrich for embryos using a mixture of cyclohexane and carbon tetrachloride (1:6), followed by drying overnight (about 14 hours). Floated wheat germ embryos (5 g) were ground in a mortar with 5 grams of powdered glass to obtain a fine powder. Extraction medium (Buffer I: 10 mM trisacetate buffer, pH 7.6, 1 nM magnesium acetate, 90 mM potassium acetate, and 1 mM DTT) was added to small portions until a smooth paste was obtained. The homogenate containing disrupted embryos and 25 ml of extraction medium was centrifuged twice at 23,000×g. The extract was applied to a Sephadex G-25 fine column and eluted in Buffer 11 (10 mM trisacetate buffer, pH 7.6, 3 mM magnesium acetate, 50 mM potassium acetate, and 1 mM DTT). A bright yellow band migrating in void volume and was collected (S-23) as one ml fractions which were frozen in liquid nitrogen.

Preparation of template: Template DNA was prepared by linearizing plasmid pSP72-bop with EcoRI. Restricted linear template DNA was purified by phenol extraction and DNA precipitation. Large scale mRNA synthesis was carried out by in vitro transcription using the SP6-ribomax system (Promega; Madison, Wis.). Purified mRNA was denatured at 67° C. for 10 minutes immediately prior to use.

Example 4

Cell-Free Translation Reactions.

The incorporation mixture (100 µl) contained 50 µl of S-23 extract, 5 mM magnesium acetate, 5 mM Tris-acetate, pH 7.6, 20 mM Hepes-KOH buffer, pH 7.5; 100 mM potassium acetate, 0.5 mM DTT, 0.375 mM GTP, 2.5 mM ATP, 10 mM creatine phosphate, 60 µg/ml creatine kinase, and 100 µg/ml mRNA containing the genetic sequence which codes for bacterio-opsin. Misaminoacylated PCB-lysine or coumarin amino acid-tRNA$^{lys}$ molecules were added at 170 µg/ml and concentrations of magnesium ions and ATP were optimized. The mixture was incubated at 25° C. for one hour.

Example 5

Isolation of Nascent Proteins Containing PCB-Lysine.

Streptavidin coated magnetic Dynabeads M-280 (Dynal; Oslo, Norway), having a binding capacity of 10 µg of biotinylated protein per mg of bead. Beads at concentrations of 2 mg/ml, were washed at least 3 times to remove stabilizing BSA. The translation mixture containing PCB-lysine incorporated into nascent protein was mixed with streptavidin coated beads and incubated at room temperature for 30 minutes. A magnetic field was applied using a magnetic particle concentrator (MPC) (Dynal; Oslo, Norway) for 0.5–1.0 minute and the supernatant removed with pipettes. The reaction mixture was washed 3 times and the magnetic beads suspended in 50 µl of water.

Photolysis was carried out in a quartz cuvette using a Black-Ray longwave UV lamp, Model B-100 (UV Products, Inc.; San Gabriel, Calif.). The emission peak intensity was approximately 1100 µW/cm$^2$ at 365 nm. Magnetic capture was repeated to remove the beads. Nascent proteins obtained were quantitated and yields estimated at 70–95%.

Example 6

Determination of the Lower Limit of Detection Using Fluorescence.

Bovine serum albumin (BSA), suspended at 0.25 mg/ml in borate buffer, pH 8.0, was combined with a 25 fold molar excess fluorescamine (Sigma Chemical; St. Louis, Mo.) at 50 mg/ml to produce a modified, fluorescent BSA. Various amounts of modified protein (1 ng, 5 ng, 10 ng, 25 ng, 50 ng, 75 ng, 100 ng, 150 ng, 200 ng) were suspended in loading buffer (bromophenol blue, glycerol, 2-mercaptoethanol, Tris-HCl, pH 6.8, SDS), and added to individual wells of a 1.5 mm thick, 12% polyacrylamide gel with a 3% stacker. The water cooled gel was electrophoresed for 4 hours at 50 volts. After electrophoresis, the gel was removed from the electrophoresis apparatus, placed on a UV transilluminator and photographed with polaroid Type 667 film using an exposure time of 10 seconds. The lowest limit of detection observed under theses conditions was 10 ng. These results indicate that using equipment found in a typical molecular biology lab, fluorescently labeled proteins can be detected at ng quantities. Using even more sophisticated detection procedures and devices the level of detection can be increased even further.

Example 7

Identification of Nascent Proteins Containing Coumarin-Amino Acid.

Cell-free translation is performed as described using charged tRNA$^{lys}$ molecules misaminoacylated with lysine coupled to a benzopyrene fluorophore moiety and human γ-interferon mRNA which contains 21 codons for lysine. Samples of the mixture are supplemented with buffer containing bromophenol blue, glycerol, 2-mercaptoethanol, Tris-HCl, pH 6.8, and SDS, and directly applied to a 12% polyacrylamide gel (3% stacker) along with a set of molecular weight markers.

Electrophoresis is performed for 3 hours at 50 volts. The gel is removed from the electrophoresis apparatus and photographed under UV light. Bands of fluorescently labeled interferon protein are specifically detected at a molecular weight of about 25 KDa. No other significant fluorescent activity is observed on the gel. Free misaminoacylated tRNA molecules may be electrophoresed off of the gel and not specifically detected.

Example 8

Determination of the In Vivo Half-Life of a Pharmaceutical Composition.

Cell-free translation reactions are performed by mixing 10 µl of PCB-coumarin amino acid-tRNA$^{leu}$, prepared by chemical misaminoacylation as described above and suspended in TE at 1.7 mg/ml), 50 µl of S-23 extract, 10 µl water and 10 µl of a solution of 50 mM magnesium acetate, 50 mM Tris-acetate, pH 7.6, 200 mM Hepes-KOH buffer, pH 7.5; 1 M potassium acetate, 5 mM DTT, 3.75 mM GTP, 25 mM ATP, 100 mM creatine phosphate and 600 µg/ml creatine kinase. This mixture is kept on ice until the addition of 20 µl of 500 µg/ml human IL-2 mRNA (containing 26 leucine codons) transcribed and isolated from recombinant IL-2 cDNA. The mixture is incubated at 25° C. for one hour and placed on ice. 100 µl of streptavidin coated magnetic Dynabeads (2 mg/ml) are added to the mixture which is placed at room temperature for 30 minutes. After incubation, the mixture is centrifuged for 5 minutes in a microfuge at 3,000×g or, a magnetic field is applied to the solution using a MPC. Supernatant is removed and the procedure repeated three times with TE. The final washed pellet is resuspended in 50 µl of 50 mM Tris-HCl, pH 75 and transferred to a quartz cuvette. UV light from a Black-Ray longwave UV lamp is applied to the suspension for approximately 1 second. A magnetic field is applied to the solution with a MPC for 1.0 minute and the supernatant removed with a pipette. The supernatant is sterile filtered and mixed with equal volumes of sterile buffer containing 50% glycerol, 1.8% NaCl and 25 mM sodium bicarbonate. Protein concentration is determined by measuring the O.D.$_{260}$.

0.25 ml of the resulting composition is injected i.v. into the tail vein of 2 Balb/c mice at concentrations of 1 mg/ml. Two control mice are also injected with a comparable volume of buffer. At various time points (0, 5 minutes, 15 minutes, 30 minutes, 60 minutes, 2 hours and 6 hours), 100 µl serum samples are obtained from foot pads and added to 400 µl of 0.9% saline. Serum sample are added to a solution of dynabeads (2 mg/ml) coated with anti-coumarin antibody and incubated at room temperature for 30 minutes. A magnetic field is applied to the solution with a MPC for 1 minute and the supernatant removed with a pipette. Fluorescence at 470 nm is measured and the samples treated with monoclonal antibody specific for rat IL-2 protein. IL-2 protein content is quantitated for each sample and equated with the amount of fluorescence detected. From the results obtained, in vivo IL-2 half-life is accurately determined.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

The invention claimed is:

1. A method for detecting nascent proteins synthesized in a translation system comprising the steps of:
   a) misaminoacylating a tRNA molecule with a non-radioactive marker;
   b) introducing the misaminoacylated tRNA to a translation system, wherein said translation system comprises nucleic acid corresponding to a disease-related gene;
   c) incubating the system to incorporate marker into a nascent protein corresponding to at least a portion of said nucleic acid; and
   d) detecting said nascent protein containing said marker.

2. The method of claim 1, wherein said disease-related gene is the APC gene and said disease is familial adenomatous polyposis.

3. The method of claim 1, wherein the translation system comprises a cellular or cell-free translation system.

4. The method of claim 3, wherein the cellular translation system is selected from the group consisting of tissue culture cells, isolated primary cells, isolated immortalized cells, isolated human cells and combinations thereof.

5. The method of claim 3, wherein the cell-free translation system is selected from the group consisting of *Escherichia coli* lysates, wheat germ extracts, insect cell lysates, rabbit reticulocyte lysates, rabbit oocyte lysates, dog pancreatic lysates, human cell lysates, mixtures of purified or semi-purified translation factors and combinations thereof.

6. The method of claim 3, wherein the cell-free translation system is a continuous flow system.

7. The method of claim 1, wherein said marker has a detectable electromagnetic spectrum.

8. The method of claim 1, wherein said marker has a defined mass.

9. The method of claim 1, wherein said marker is a photocleavable marker which is cleaved by electromagnetic radiation.

10. The method of claim 9, wherein the electromagnetic radiation is selected from the group consisting of x-rays, ultraviolet rays, visible light, infrared rays, microwaves, radio waves, electric fields and combinations thereof.

11. The method of claim 1, wherein the tRNA molecule is aminoacylated by chemical misaminoacylation.

12. The method of claim 1, wherein two or more different misaminoacylated tRNAs are introduced to the translation system.

13. The method of claim 1, wherein said nascent protein is detected by spectrometry.

14. The method of claim 1, wherein the tRNA molecule is an initiator tRNA molecule.

15. The method of claim 1, wherein the tRNA molecule is a suppressor tRNA molecule.

16. The method of claim 1, further comprising the step of isolating said nascent protein containing said marker.

17. The method of claim 16, wherein said nascent protein is isolated by a process selected from the group consisting of electrophoresis, electroelution, precipitation, chemical extraction, chromatography, magnetic separation and combinations thereof.

18. A method for detecting nascent proteins synthesized in a translation system comprising the steps of:
   a) misaminoacylating a tRNA molecule with a non-radioactive marker;
   b) introducing the misaminoacylated tRNA to a translation system, wherein said translation system comprises nucleic acid corresponding to a disease-related gene having a reading frame, wherein said nucleic acid contains a stop codon within said reading frame;
   c) incubating the system to incorporate marker into a truncated nascent protein corresponding to the portion of said nucleic acid prior to said stop codon; and
   d) detecting said truncated nascent protein containing said marker.

19. The method of claim 18, wherein said disease-related gene is the APC gene and said disease is familial adenomatous polyposis.

20. The method of claim 18, wherein the translation system comprises a cellular or cell-free translation system.

21. The method of claim 18, wherein said marker is a photocleavable marker which is cleaved by electromagnetic radiation.

22. The method of claim 18, further comprising the step of isolating said truncated nascent protein containing said marker.

23. The method of claim 22, wherein said nascent protein is isolated by a process selected from the group consisting of electrophoresis, electroelution, precipitation, chemical extraction, chromatography, magnetic separation and combinations thereof.

* * * * *

```
SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
         (A) LENGTH: 5 amino acids
         (B) TYPE: amino acid
         (C) STRANDEDNESS: not relevant
         (D) TOPOLOGY: not relevant (ii) MOLECULE TYPE: protein (xi) SEQUENCE DESCRIPTION: SEQ ID NO: 1:

Ala Val Tyr Lys Trp
1               5

(2) INFORMATION FOR SEQ ID NO: 2:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO: 2:

AUGUACACUA AACAUGAUGA UAUCCGAAAA UGA                              33

(2) INFORMATION FOR SEQ ID NO: 3:

(i) SEQUENCE CHARACTERISTICS:
         (A) LENGTH: 10 amino acids
         (B) TYPE: amino acid
         (C) STRANDEDNESS: not relevant
         (D) TOPOLOGY: not relevant (ii) MOLECULE TYPE: protein (ix) FEATURE:
         (A) NAME/KEY: Modified-site
         (B) LOCATION: 1
         (D) OTHER INFORMATION: /note= "The amino acid in this
             position is N-formylmethionine"

(xi) SEQUENCE DESCRIPTION: SEQ ID NO: 3:

Met Tyr Thr Lys Asp His Asp Ile Arg Lys
1               5                   10

(2) INFORMATION FOR SEQ ID NO: 4:
```

```
    (i) SEQUENCE CHARACTERISTICS:
        (A) LENGTH: 10 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 10
        (D) OTHER INFORMATION: /note= "The amino acid at this
             position is N-formylmethionine"

(xi) SEQUENCE DESCRIPTION: SEQ ID NO: 4:

Lys Arg Ile Asp Asp His Lys Thr Tyr Met
1               5                   10
```